(12) United States Patent
Johnson et al.

(10) Patent No.: US 7,119,337 B1
(45) Date of Patent: Oct. 10, 2006

(54) INFRARED RADIATION SOURCES, SENSORS AND SOURCE COMBINATIONS, AND METHODS OF MANUFACTURE

(75) Inventors: Edward A. Johnson, Bedford, MA (US); John S. Wollam, Acton, MA (US); James T. Daly, Mansfield, MA (US)

(73) Assignee: Ion Optics, Inc., Waltham, MA (US)

( * ) Notice: Subject to any disclaimer, the term of this patent is extended or adjusted under 35 U.S.C. 154(b) by 0 days.

(21) Appl. No.: 09/762,077

(22) PCT Filed: Jul. 30, 1999

(86) PCT No.: PCT/US99/17338

§ 371 (c)(1),
(2), (4) Date: Jun. 3, 2002

(87) PCT Pub. No.: WO00/07411

PCT Pub. Date: Feb. 10, 2000

Related U.S. Application Data

(63) Continuation-in-part of application No. 08/905,599, filed on Aug. 4, 1997, now Pat. No. 5,838,016.

(60) Provisional application No. 60/094,602, filed on Jul. 30, 1998.

(51) Int. Cl.
*G01J 5/02* (2006.01)

(52) U.S. Cl. .......................... 250/339.13; 250/504 R; 250/495.1

(58) Field of Classification Search ............ 250/504 R, 250/339.13
See application file for complete search history.

(56) References Cited

U.S. PATENT DOCUMENTS

| | | | |
|---|---|---|---|
| 4,620,104 A | 10/1986 | Nordal et al. | 250/493.1 |
| 4,644,141 A | 2/1987 | Hagen et al. | 219/543 |
| 4,859,858 A | 8/1989 | Knodle et al. | 250/504 |
| 4,876,413 A | 10/1989 | Vermilyea | 174/15.4 |
| 4,926,992 A | 5/1990 | Linnig | 192/48.2 |

(Continued)

OTHER PUBLICATIONS

Hutley, M.C. et al., The Total Absorption of Light By A Difraction Grating, Optics Communications, 19(3), 431-36, Dec. 1976.
Loewen, E. G. et al., Dielectric Coated Gratings: A Curious Property, Applied Optics, 16(11), 3009-11, Nov. 1977.

(Continued)

*Primary Examiner*—John R. Lee
*Assistant Examiner*—Phillip Johnston
(74) *Attorney, Agent, or Firm*—McDermott Will & Emery LLP

(57) ABSTRACT

A blackbody radiation device (110) includes a planar filament emission element (102) and a planar detector (104) for respectively producing and detecting radiation having width dl/1 less than about 0.1 to test a sample gas, where 1 is the wavelength of the radiation; a reflector (108); a window (W); an electrical control (118); and a data output element (116).

27 Claims, 44 Drawing Sheets

U.S. PATENT DOCUMENTS

| | | | |
|---|---|---|---|
| 5,060,508 A | 10/1991 | Wong | 73/31.02 |
| 5,074,490 A | 12/1991 | Muse et al. | 244/3.11 |
| 5,128,514 A | 7/1992 | Lehmann et al. | 219/209 |
| 5,220,173 A | 6/1993 | Kanstad | 250/493.1 |
| 5,324,951 A | 6/1994 | Kocache et al. | 250/493.1 |
| 5,444,249 A | 8/1995 | Wong | 250/343 |
| 5,584,557 A * | 12/1996 | Alexay | 362/552 |
| 5,754,290 A | 5/1998 | Rajic et al. | 356/328 |
| 5,838,016 A | 11/1998 | Johnson | 250/504 R |
| 5,864,144 A * | 1/1999 | Laine | 250/504 R |
| 6,297,511 B1 * | 10/2001 | Syllaios et al. | 250/495.1 |

OTHER PUBLICATIONS

Rajic, S. et al., Design, Fabrication, and Testing of Micro-Optical Sensors Containing Multiple Aspheres, SPIE, 2536, 452-62, (1995).

Gupta, Sandhya et al., Infrared Filters Using Metallic Photonic Band Gap Structures On Flexible Substrates, Appl. Phys. Lett. 71(17), 2412-14, Oct. 27, 1997.

Rehse, S.J. et al., Nanolithography With Metastable Neon Atoms: Enhanced Rate of Contamination Resist Formation for Nanostructure Fabrication, Appl. Phys. Lett., 71(10), Sep. 8, 1997.

* cited by examiner

INFRARED RADIATION SOURCES, SENSORS AND SOURCE COMBINATIONS, AND METHODS OF MANUFACTURE

RELATED APPLICATIONS

This application is a continuation-in-part of commonly owned and U.S. patent application Ser. No. 08/905,599, filed on Aug. 4, 1997, now U.S. Pat. No. 5,838,016, granted Nov. 17, 1998, and U.S. Provisional Patent Application Ser. No. 60/094,602, filed on Jul. 30, 1998, and PCT Application No. PCT/US98/25771, filed Dec. 4, 1998, International Publication No. WO99/28729, which are all hereby expressly incorporated by reference. Related PCT Application No. US99/07781, filed Apr. 9, 1999, is an appendix to this application.

FIELD OF THE INVENTION

This invention relates to optical radiation sources and relates in particular to blackbody radiation sources whose wavelength-dependent surface emissivity is modified in order to radiate with higher power efficiency and/or to radiate within a desired wavelength controlled spectral band. The invention also relates to sensors incorporating sources and to systems and methods embodying same.

BACKGROUND OF THE INVENTION

Non-dispersive Infrared (NDIR) techniques utilizing the characteristic absorption bands of gases in the infrared have long been considered as one of the best methods for gas measurement. These techniques take advantage of the fact that various gases exhibit substantial absorption at specific wavelengths in the infrared radiation spectrum. The term "non-dispersive" refers to the type of apparatus incorporating the NDIR technique, typically including a narrow band pass interference filter (as opposed to a "dispersive" element such as a prism or a diffraction grating to isolate and pass radiation in a particular wavelength band from a spectrally broad band infrared source. The gas concentration is discerned from the detected intensity modulation of source radiation emanating from the source and passed by the filter coincident in wavelength with a strong absorption band of the gas to be measured.

A prior art NDIR gas analyzer typically includes an infrared source with a motor-driven mechanical chopper to modulate the source so that synchronous detection is used to discriminate spurious infrared radiation from surroundings; a pump to push gas through a sample chamber; a narrow band-pass interference filter; a sensitive infrared detector, inexpensive infrared optics and windows to focus the infrared energy from the source onto the detector. Despite the fact that the NDIR gas measurement technique is one of the best methodologies that had ever been devised, it has not enjoyed wide application because of its complexity and high cost of implementation.

Several components play essential roles in making the NDIR technique work for gas measurement. The radiation source is one such component; and in order for NDIR methodology to work efficaciously, this source must provide broad spectral output and give high power in the band of interest. A blackbody radiation source is generally used for this component because it can be heated to a temperature that provides high intensity radiation within any wavelength region. Because the blackbody output spectral distribution and intensity are uniquely determined by the temperature of the source, the spectral peak intensity can be adjusted by varying the temperature of the blackbody source. By the well-known Wien's Displacement Law the peak intensity of a blackbody radiation source of temperature T is at a wavelength $\lambda_{max}$ equivalent to $2.898 \times 10^{-3}/T$ where T is measured in degrees Kelvin (1° K) and $\lambda_{max}$ is measured in meters. By the process of T and the size of the blackbody radiator, a desired intensity of blackbody radiation selected wavelength $\lambda$ can be attained.

The so-called "Nernst Glower," consisting of a heating element of a tungsten filament) embedded in a ceramic slab, has long been used for the blackbody source of most prior art NDIR gas detection systems. Despite the fact that the Nernst Glower gives off an amount of infrared energy with an emissivity close to unity, its power efficiency (i.e., efficiency from electrical to useable optical energy) is notoriously low. The large amount of unwanted heat is also a major drawback in the use of the Nernst Glower in any NDIR gas measurement systems. Furthermore, the large heat capacity of the Nernst Glower makes it a necessarily slow device in terms of intensity modulation. In many cases, it can only be used as a steady state or DC radiation source; and thus a mechanical chopper is needed to generate synchronous modulated signals, further adding to the complexity of NDIR gas measurement systems.

The prior art has attempted to replace the blackbody radiator with hot filament as an approximation to a blackbody. However, such a filament does not have high emission over all wavelengths because there is spatial temperature variation within the filament; it is not an ideal blackbody source. Optical radiation sources, such as a hot filament lamp, are thus often referred to as "quasi-blackbody" sources. In addition, hot filament radiators typically are used by a quartz bulb which is substantially opaque for wavelengths, longer than about 4.5 μm reducing its applicability to gas detection through longer wavelength absorption lines. Prior art hot filaments are thus not particularly good infrared radiation sources for use with NDIR gas sensors.

The prior art has attempted to improve NDIR sensors. In U.S. Pat. No. 4,876,413 (the '414 patent), published in April of 1975, Bridgham describes an infrared radiation source that includes a thin film resistor heater with highly emissive material $Cr_3Si$ on a substrate. The thin film heater is positioned between a pair of thin metal elements serving as sensing electrodes on a very thin (<0.005" typical) insulating substrate. The entire thin film heater is packaged in a standard TO-5 heater equipped with a focusing reflector and pins supporting the heater structure.

While the source of the '413 patent advances infrared radiator sources in terms of higher emissivity and wider spectral emissions, it does not offer size or speed advance over the classic tungsten lamp. Furthermore, its construction is rather fragile and the heater cannot withstand temperatures above −700° C., severely limiting the maximum allowable output. Finally, its overall power efficiency is rather poor and the low cost and useable life of this radiator has not been satisfactorily proven. Consequently, the source of the '413 patent has not found wide application in NDIR gas measurement systems.

In U.S. Pat. No. 4,644,141 published in February of 1987, Hager et al. advances a heater structure first proposed in the '413 patent, except that a combination of silicon, silicon oxides and a platinum metal pattern are used as the heating element to optimize the performance of the overall heater structure. Nevertheless, other than a slight improvement in power efficiency over the device of '413 patent, there is no fundamental advancement over the prior art.

Over the past several years, significant technical progress has been made in the area of optical sources as set forth in the inventor's own prior application of U.S. Ser. No. 08/511,070, filed on Aug. 3, 1995. Such optical sources have greatly increased the reliability and cost-effectiveness of NDIR gas sensors.

The present invention has several objects in providing further improvements and advantages in source and sensor embodiments as compared to the prior art. One object of the invention is to provide sources which function as tuned waveband emitters that preferentially emit radiation into a wavelength band of interest as compared to blackbody or gray-body radiators. Another object of the invention provides in integrated circuit sensor include selectively tuned radiation source. Still another object of the invention provides methods and devices for sensing gas constituents without certain of the difficulties and problems of prior art NDIR devices.

These and other objects will become apparent in the description which follows.

SUMMARY OF THE INVENTION

As used herein, "on chip" refers to integrated circuits and the like which are processed through microelectronic fabrication techniques to provide circuitry and/or processes (including A/D processing) on a semiconductor element or chip.

As used herein, "SOURCE" generally means tuned waveband emitters constructed according to the invention that preferentially emit radiation into a wavelength band of interest. Certain SOURCES, for example, include those tuned radiation sources described in the commonly assigned and copending U.S. Ser. No. 08/905,599, filed on Aug. 4, 1997, now U.S. Pat. No. 5,838,016, granted Nov. 17, 1998, and U.S. Ser. No. 08/511,070, filed on Aug. 3, 1995, now abandoned (the latter also being incorporated herein by reference). Still other SOURCES including tuned cavity emitters, chemical and microelectronic/semiconductor emitters, and other etched electro-mechanical, chemically-treated, ion-bombarded and lithographically created surfaces which permit spectral control and which provide narrow band incoherent emissions tailored to specific end-user needs and requirements.

The invention has many objectives in providing improved sources and sensors. It also utilizes and is complimentary to certain art encompassing other areas including NDIR gas measurement technology, silicon micro-machined thermopile, optical beam configurations and fabrication techniques. As such, the following patents and publications providing information and background to the specification and are herein incorporated by reference. U.S. Pat. No. 4,620,104; U.S. Pat. No. 4,644,141; U.S. Pat. No. 4,859,858; U.S. Pat. No. 4,926,992; U.S. Pat. No. 5,060,508; U.S. Pat. No. 5,074,490; U.S. Pat. No. 5,128,514; U.S. Pat. No. 5,152,870; U.S. Pat. No. 5,220,173; U.S. Pat. No. 5,324,951; U.S. Pat. No. 5,444,249,249; Hutley et al., *The Total Absorption Of Light By A Diffractive Grating*, Optics Communications, 19(3), pp. 431–436 (1976); Loewen et al., *Dielectric Coated Gratings: A Curious Property*, Applied Optics, Vol. 16(11), pp. 3009–3011 (1977); Rajic et al., *Design, Fabrication, And Testing Of Micro-Optical Sensors Containing Multiple Aspheres*, SPIE, Vol. 2356, pp. 452–462 (1995); Gupta et al., *Infrared Filters Using Metallica Photonic Band Gap Structures On Flexible Substrates*, Appi Phys. Lett., 71(17), pp. 2412–2444 (1997); and Rehse et al., *Nanolithograhy With Metastable Iron Atoms: Enhanced Rate Of Contamination Resist Formation For Nanostructure Fabrication*, Appl. Phys. Lett., 71(10), pp. 1427–1429 (1997).

In one aspect, the invention provides an integrated circuit sensor (ICS). The ICS has a tuned narrow band emitter (e.g., a SOURCE of the invention) and a tuned narrow band detector fabricated on a single silicon die, Optics (e.g., reflective optics or a silicon slab waveguide) capture source emissions and refocus the captured energy onto the detector. Control electronics are preferably included and are preferably incorporated "on chip" to facilitate packaging issues. A solar cell can also be integrated with the sensor to provide power. The sensor can further be integrated with other features described herein or contained in related applications.

In another aspect, the invention provides a Hybrid Infrared Gas and Thermal Sensor Head ("HIRGS"). A SOURCE is integrated with an uncooled detector (e.g., a microbolometer detector), and a reflector (e.g., a parabolic reflector) into a package such as a single transistor can. Source drive electronics and detector readout electronics and preferably included with the HIRGS and can also be provided "on chip". The detector is also preferably "tuned" to the waveband emissions of the SOURCE.

In still another aspect, the invention provides an Integrated Gas Sensor ("IGS"). A SOURCE is coupled to illumination optics which pass a beam (of tuned magnetic radiation) into a gas sample or stream. A detector (preferably with receiving optics) is arranged to capture the beam and convert the beam into electrical signals. An electronics system is used to diagnose the beam intensity and spectral characteristics to analyze the gas, e.g., to determine the % concentration of a particular gas.

In another aspect, an alternative IGS includes a SOURCE which incorporates a gas cell sample (or gas flow cell). Wavelength compatible optics preferably collect SOURCE emissions to efficiently illuminate the cell. A mirror (e.g., a flat mirror) positioned on the opposite side of the cell reflects the SOURCE emissions back through the cell and to a detector (also preferably with optics to improve collection efficiency). The detector is positioned to collect the reflected beam adjacent to the SOURCE. An electronics subsystem is used to diagnose the beam intensity and spectral intensities to determine characteristics of the gas, e.g., concentration of a particular gas.

In one aspect, methodology is provided for manufacturing a microbolometer-based SOURCE and integrated sensor. The sensor includes one microbolometer arranged to emit tuned radiation, optics to collect and transmit the radiation to a sample under study for a specific purpose (e.g., to illuminate a gas cell or a solid surface), and another microbolometer arranged to collect at least part of the post sample (i.e., transmitted through the gas or scattered from the surface) radiation. As known in the art, microbolometers function by efficiently collecting infrared radiation within an absorbing microbridge cavity; and the absorbed energy changes the resistance of the bridge electronics, indicating an amount of radiation. The efficient thermal mass of the bridge permits very fast dissipation of radiant energy so that multiple microbolometer can efficiently take high speed IR picture frames (i.e, each microbolometer operating as a pixel in a picture in accord with the invention, the source microbolometer operates in reverse: electric energy drives the microbolometer to radiate heat and to emit radiation in the band of the cavity. The sister microbolometer detector is tuned to the same band and the two microbolometer effectively emit and recover tuned electromagnetic radiation.

In another aspect, a tuned cavity band emitter SOURCE is provided. The SOURCE of this aspect has an emissivity curve which differs—selectively and beneficially-from a standard blackbody curve. It thus functions as a selective incoherent band emitting infrared source. This SOURCE can thus include a metal foil filament such as provided in U.S. patent application Ser. No. 08/905,599; and can further include a metal transistor can be coupled to the SOURCE. The SOURCE of this aspect can also be constructed with spectral control, including supporting electronics, to function as an incoherent narrow band emitter. Preferably, the surface of the emitting SOURCE of this aspect is dark. It also includes a sharp spectral transition between a high absorbing band and a highly reflecting out of band, thereby functioning as a "band emitter".

By way of background, prior art incoherent sources radiate in a manner representative of a blackbody curve. However, most applications and products utilize only a small band within the spectrum relative to that blackbody curve (by way of example, most devices are used to generate energy within a defined band; and other radiation can result in noise). These prior art sources thus inefficiently emit energy into the band. Accordingly, when the prior art source is brought to temperature, the blackbody emissions at the center of the measurement band represent only a tiny fraction of the total radiant output falls within the desired measurement band. The invention solves this dilemma.

In accord with the invention, the SOURCE emitter surface of one aspect is modified to become an effective band emitter. By suppressing out-of-band emission sensors and systems utilizing the SOURCE trade out-of-band photons (noise) for in-band photon (signal). In essence, the SOURCE becomes a near-perfect reflecting surface for out-of-band radiation and a highly efficient absorber for in-band radiation corresponding to an array of absorbers. The size, shape, and spacing of these cavities are designed to absorb at a pre-selected resonance wavelength. The size of these cavities should be about $\lambda/2\pi$ for the desired wavelength of medium and longwave infrared radiation (e.g., 3–5 µm and/or 8–12 µm), the cavity sizes are within the limits of state of the art microlithography and microfabrication techniques. Thus, this aspect of the invention includes a SOURCE with manually applied cavities disposed thereover with microlithography.

In another aspect, the invention provides mid-and long-wavelength infrared sensors for gas detector applications utilizing a non-blackbody, narrow-band radiator. The SOURCE of this aspect includes sub-micron scale surface structures which facilitate control of the radiator emission spectrum. The source thus combines blackbody radiator functionality with a surface that selectively filters wavelength emissions.

In another aspect, an optical radiation SOURCE is provided which optimizes the following three parameters for improved waveband emissions: operating temperature T(° K), emitting area A, and surface emissivity $\epsilon(\lambda)$. The SOURCE utilizes structure which emphasizes the emitting surface characteristics (e.g., cavity structure) of the radiator and which optimizes its emitting area and its emissivity to maximize power output in the optimized waveband.

Another aspect of the invention provides an optical radiation SOURCE with an output that is "spectrally tailored" relative to the emission a perfect blackbody by modifying surface emissivity so as to maximize power output in a desired and controlled spectral wavelength.

In another aspect, the optical radiation SOURCE of the invention has a thin structure with a well-defined outwardly facing surface that emits optical radiation. The thin structure includes a resistive element in the form of a thin film or foil supported by a substrate and configured with surface structure as discussed above. The optical radiator SOURCE is powered by electrical current passed through its resistive element. The texture of the outwardly facing filament is methodically and controllably modified by well-known techniques—such as electrolytic plasma etching, ion-milling, and preferably in combination with photo-lithographic masking technology—such that the emissivity of the radiator SOURCE possesses an emissivity near to unity with well-defined and controllable spectral wavelength band.

The invention is next described further in connection with preferred embodiments, and it will become apparent that various additions, subtractions, and modifications may be made by those skilled in the art without departing from the scope of the invention.

BRIEF DESCRIPTION OF THE DRAWINGS

The foregoing and other objects of this invention, the various features thereof, as well as the invention itself, may be more fully understood from the following description, when read together with the accompanying drawings in which:

FIGS. 7A(c), 7B and 7C show the emission spectra of IR sources of the invention;

FIGS. 8A and 8B of sheet 4/17 of WO 00/07411 are duplicative of step 7 and step 10 of FIG. 8A of sheet 8/17 of WO 00/07411;

DESCRIPTION OF PREFERRED EMBODIMENTS

I. Reflector Source with Reflector Housing in Front of Planar Emitter which is Normal to the Emission Axis, in Conjunction with Textured Source One form of the invention is a relatively low power reflector infrared (IR) source with an improved texture, smaller (compared to the prior art) filament, and with an integral reflector.

A common design issue for IR sources is the requirement for significantly more useful signal, particularly in the LWIR, with significantly less required drive power. The present invention effects such changes by including reduced filament size, improved filament texture, and by incorporating a reflector into the source package. This allows, for example, for medical instruments (including anesthesia monitors or critical care systems), industrial safety instruments, and automotive emission monitoring.

Figure 1A:
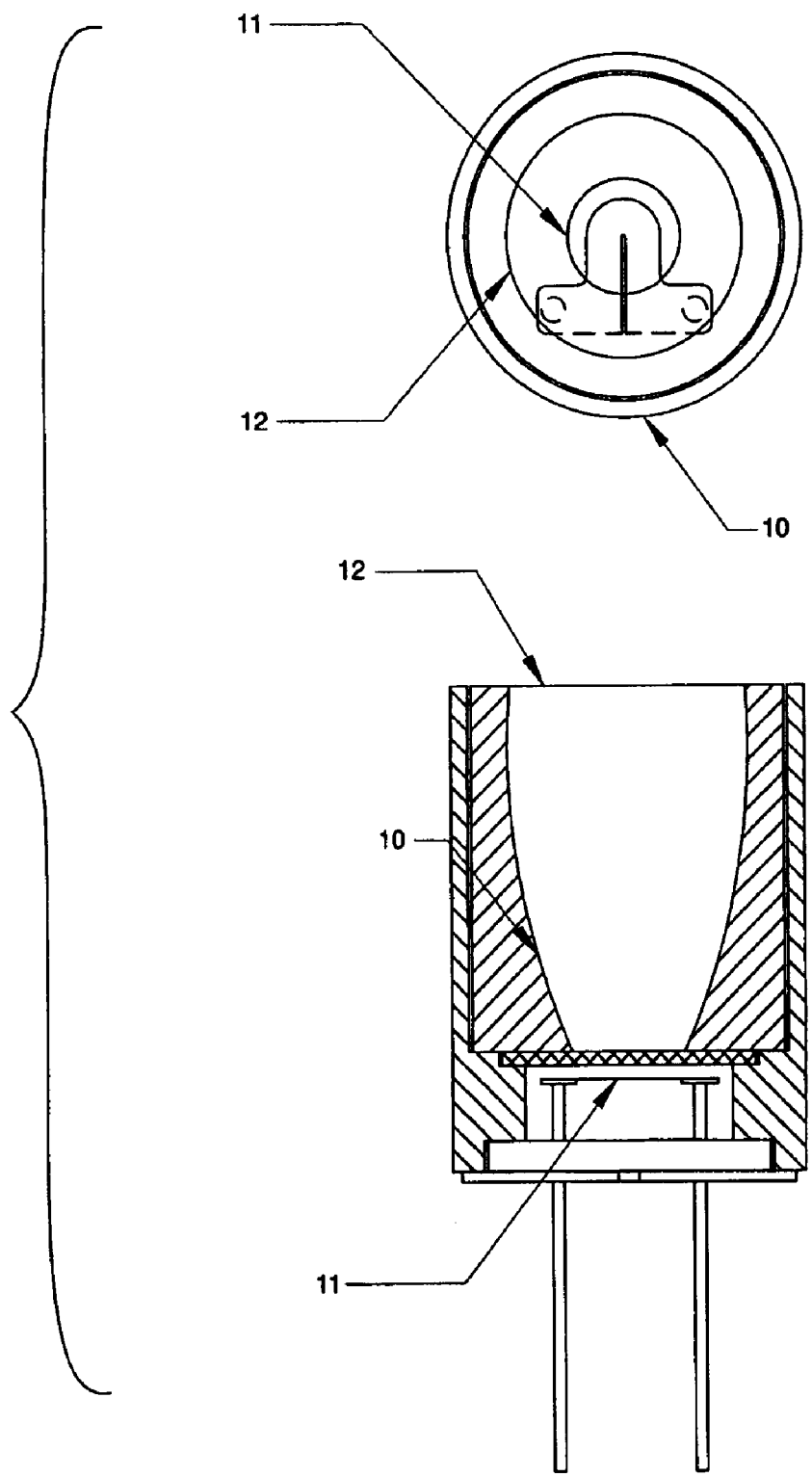
FIG. 1A shows an IR source in accordance with the invention.
Figure 1B:
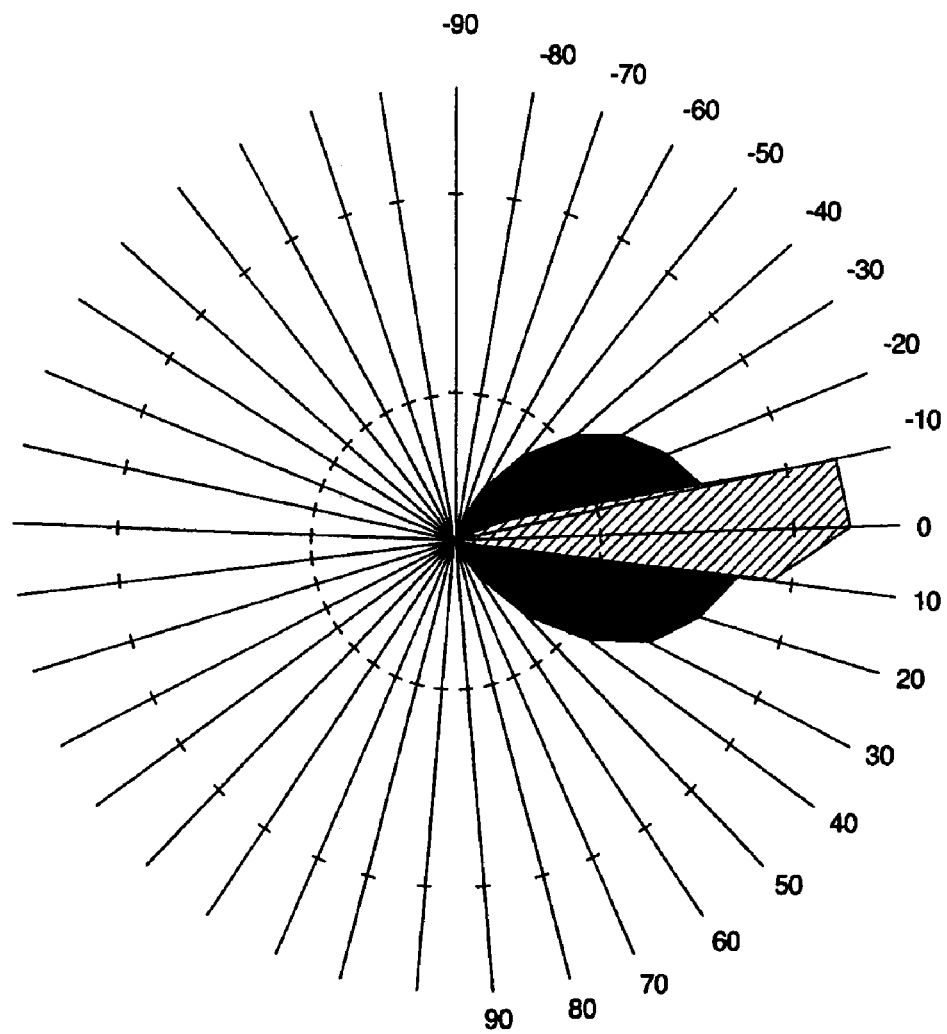
FIG. 1B shows the beam shape of the IR source of FIG. 1.
Figure 1C:
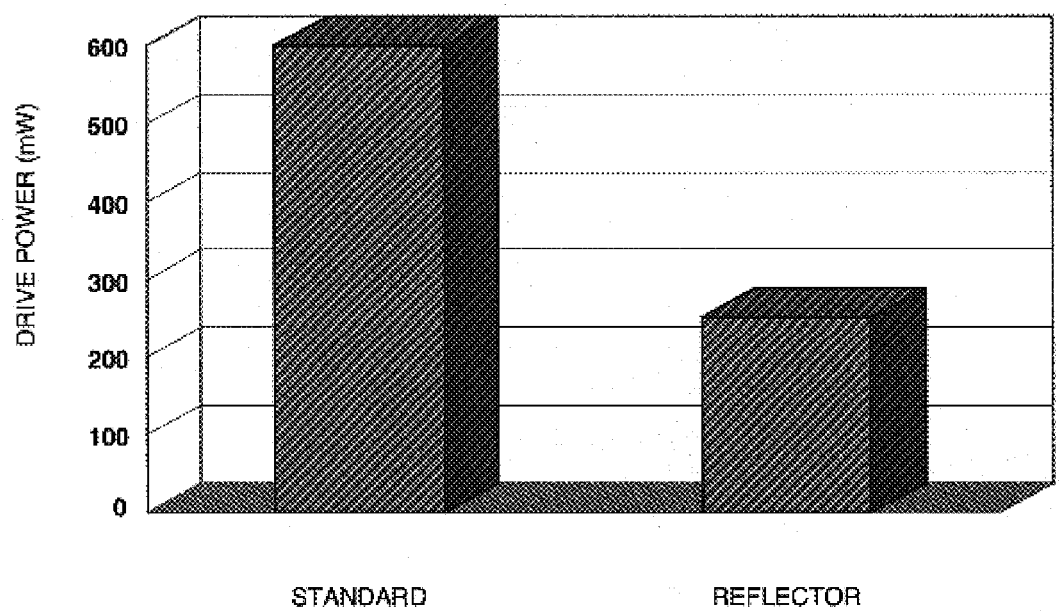
FIG. 1C shows a graphical comparison of drive power of the IR source of FIG. 1 and a standard source.

FIG. 1A shows an IR source 10 of the invention having relatively high usable signal with relatively low drive power. A relatively small filament 10 is used with a molded reflector 12 to provide a "search light" type beam-former, illuminating a narrow forward cone (as shown in FIG. 1B) and eliminating the need for discrete optical (lens) elements. The smaller filament of the invention also uses less power compared to the prior art ("standard") as shown in FIG. 1C.

This source 10 reduces the required parts count and integration complexity for instrument environments, by integrating relatively high functionality into a single component by reducing or eliminating the need for separate optical elements and providing an output illumination cone which is compatible with standard thin film interference filters.

Figure 1D:
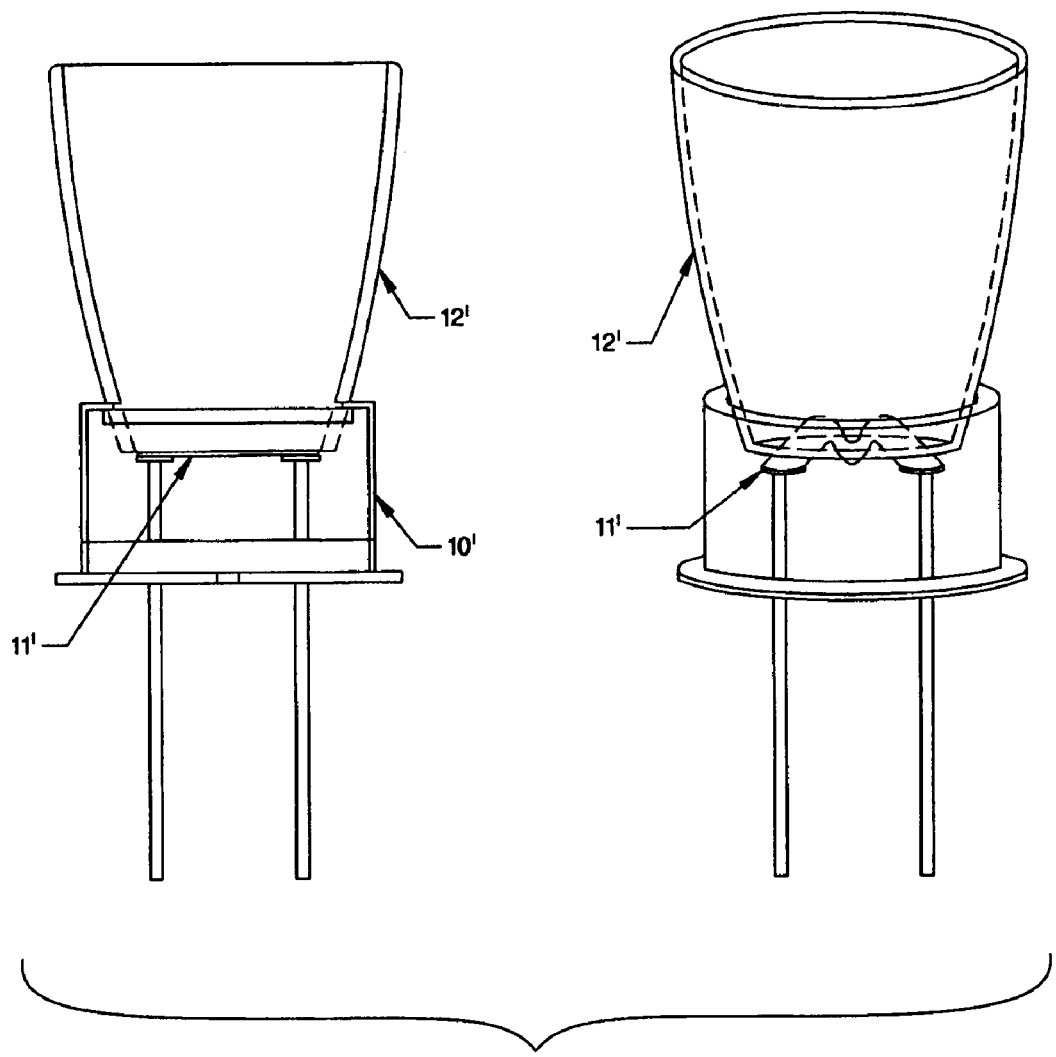
FIGS. 1D, 2 and 3A show alternative IR sources in accordance with the invention.

FIG. 1D shows an IR source 10' which is similar to source 10 but includes an "M"-shaped filament 11', and a formed-sheet reflector 12'.

This form of IR source does not require extensive tooling or automation. Preferably, the source utilizes a laser cut filament cut from thin self-supporting metal foils which are treated in large (e.g., 10 cm square) sheets. Again, preferably, the filament size is relatively small (for example, 250 parts per 10 cm square).

Figure 2:
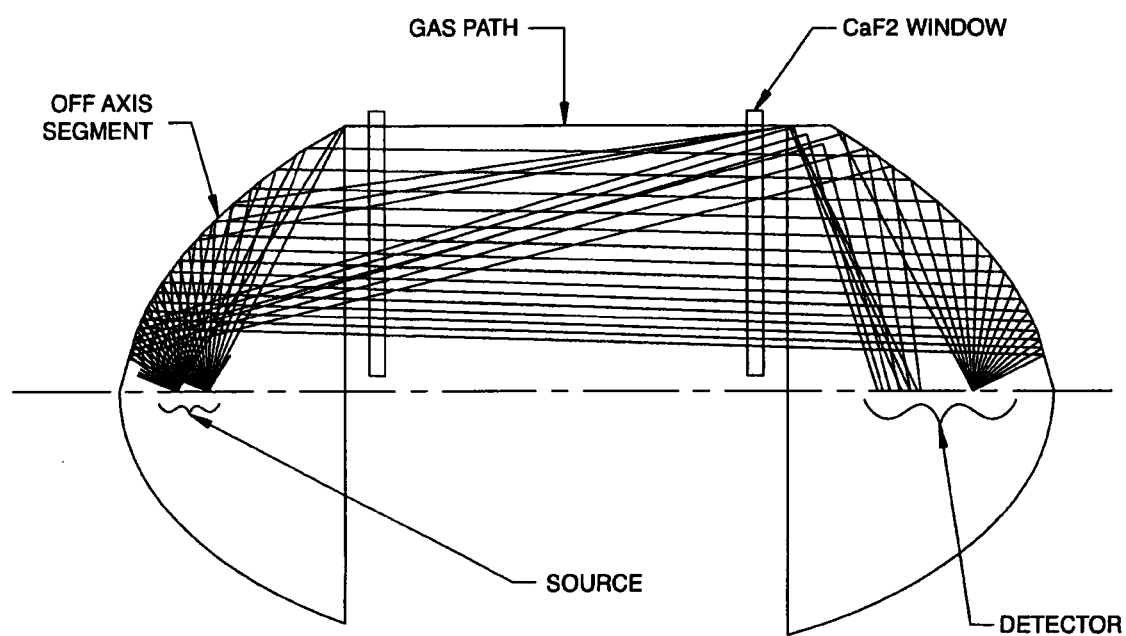
Figure 3A:
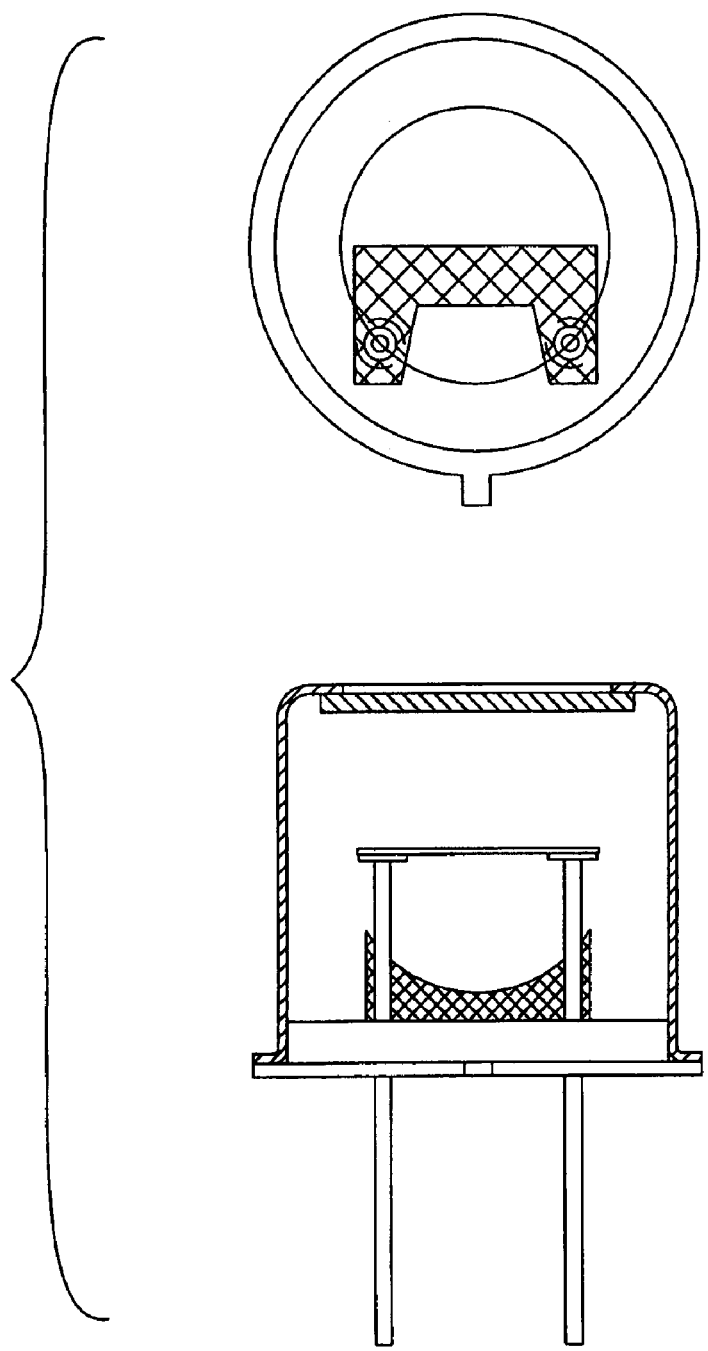
Figure 3B:
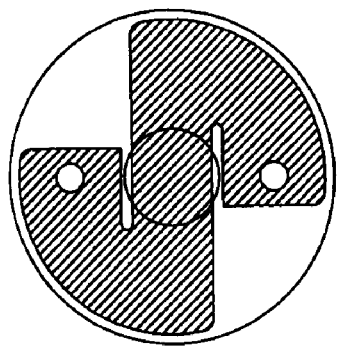
FIGS. 3B, 3C and 3D show exemplary filament emitters in accordance with the invention.
Figure 3C:
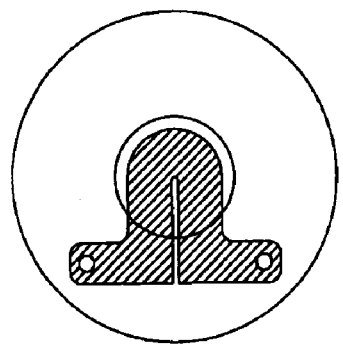
Figure 3D:
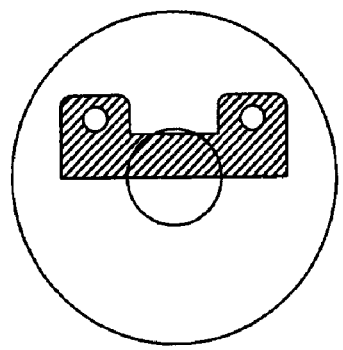

II. Radiation Source with Parabolic or Compound Parabolic "Winston" Collimator, in Conjunction with Textured Source FIG. 2 shows another exemplary form of IR source of the invention, particularly including straight parabolic, or compound parabolic collimators configured in combination with a textured source. The embodiment of FIG. 2 shows a single loop, single bar filament with a "behind the source" concentrators. FIG. 3A shows a "two-sided" emitter with a "behind the source" concentrator. FIGS. 3B–3D show exemplary filament emitters.

Figure 4:
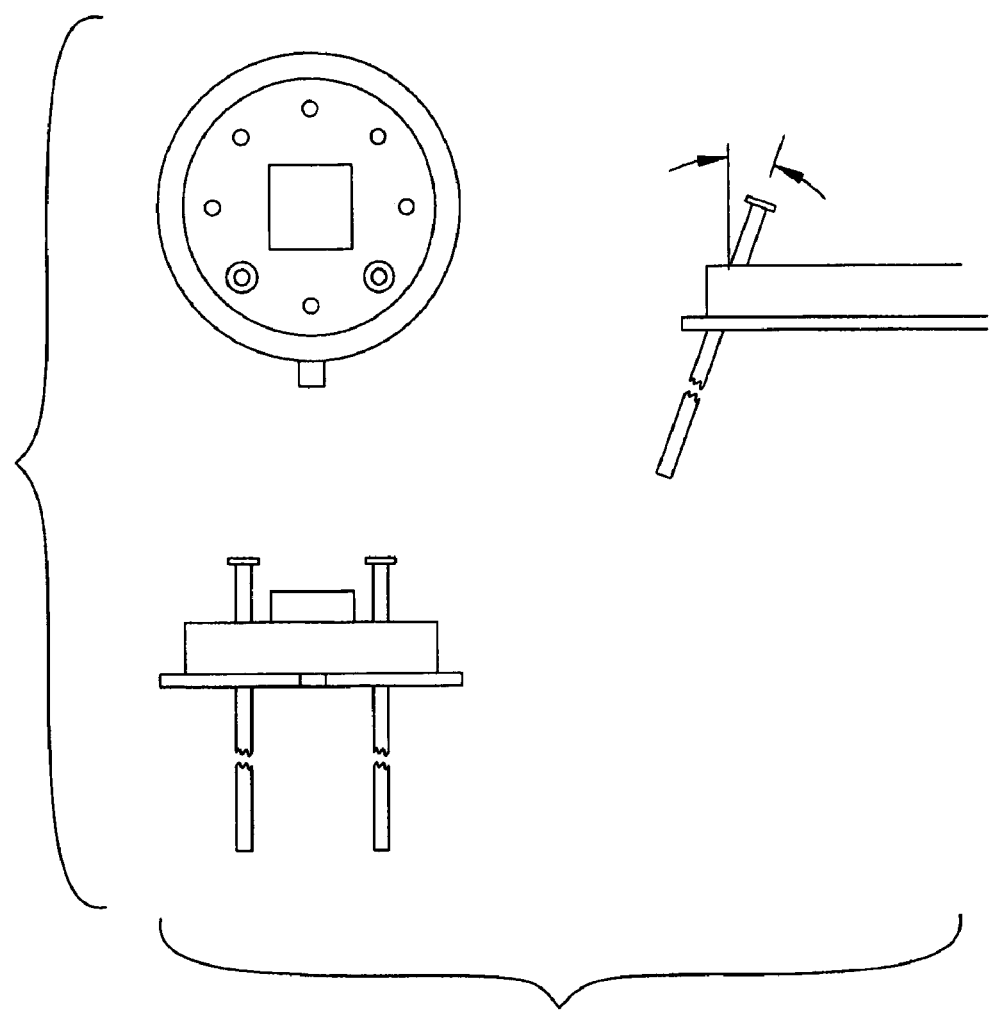
FIG. 4 shows another IR source in accordance with the invention.

FIG. 4 shows a "flat pack" construction source which allows a variety of reflector configurations. By utilizing double sided emission, the filament effectively doubles its active area and provides twice the usable in-band signal flux at a given temperature.

Figure 5:
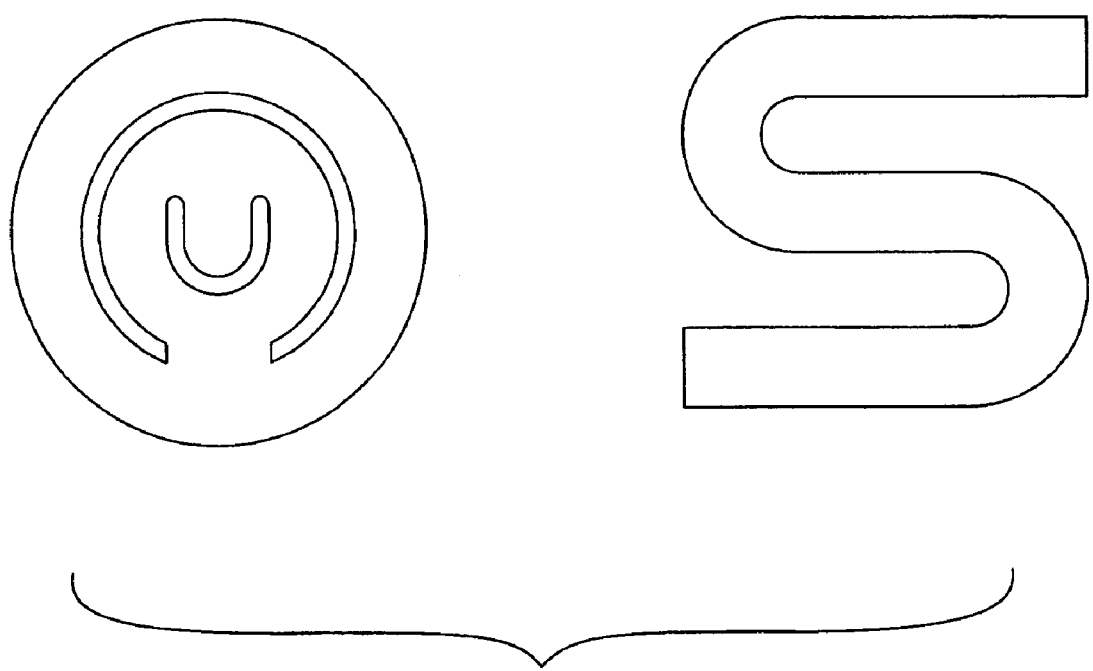
FIGS. 5 and 6 show additional exemplary emitters.
Figure 6:
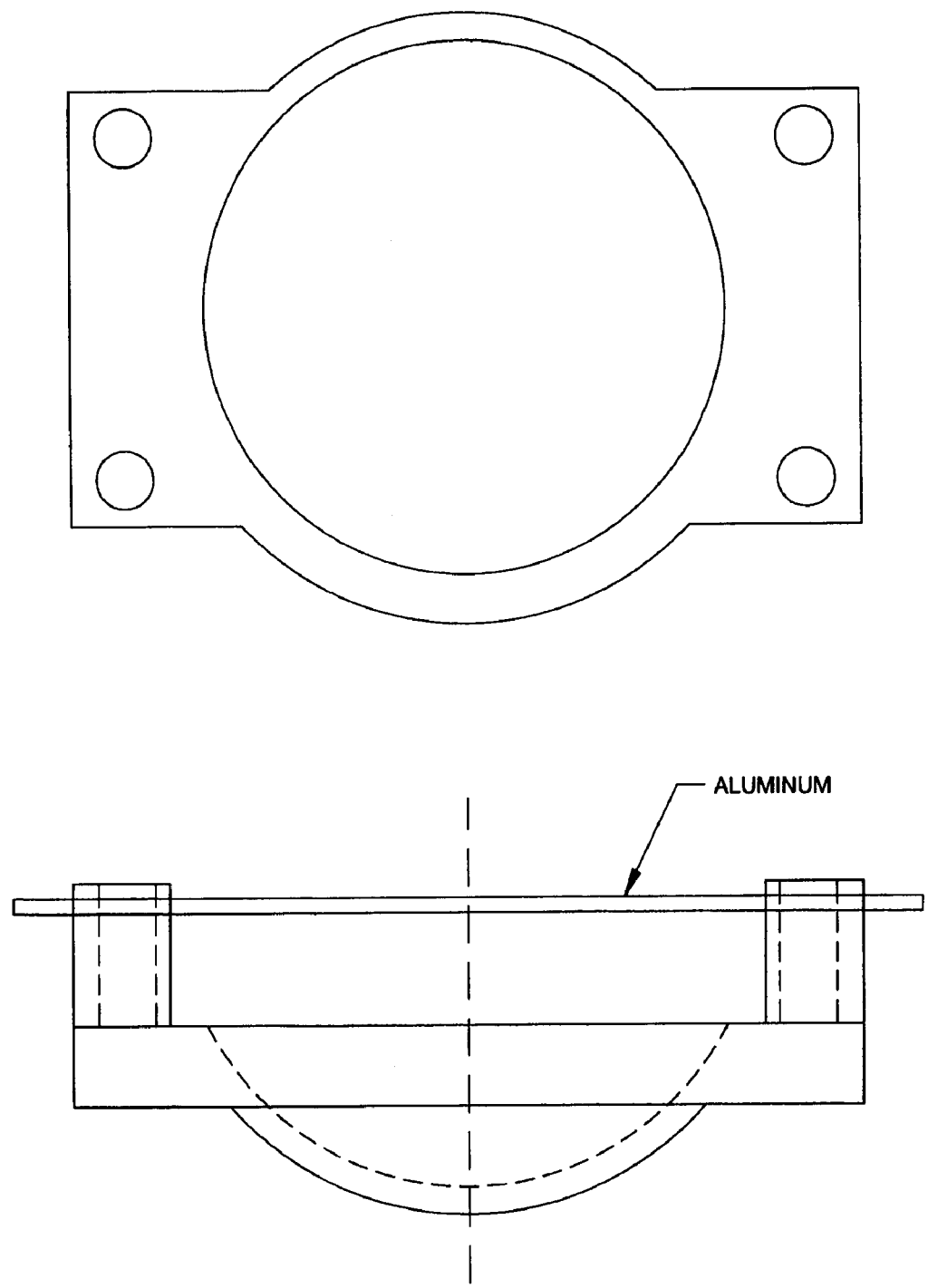

Other filament configurations provide additional "shine-through" illumination for rear-mounted reflectors, for example, as shown in FIGS. 5 and 6. In FIG. 6, the filament is "sideways", i.e., the reflector axis is in the plane of the filament.

III. Tuned Band Emitter Sources

A. Tuned Band Emitter "Photonic Band Gap" Filament

The incorporated PCT Application No. PCT/US98/25771 discloses IR sources with metal foil filaments, and particularly shows an embodiment in a Tx metal transistor can. That form of source effects spectral control, and teaches use of spectral control to construct an incoherent narrow band emitter. In the prior art, the emitting surface has been modified to make it dark, but significant spectral control has not been accomplished. In accordance with the present invention, there are sharp spectral transitions between highly absorbing, in band, and highly reflecting, out of band, thereby effecting a band emitter. Traditional incoherent sources are constrained by the blackbody curve. The blackbody curve assures that, even if the source temperature is brought to peak with the blackbody distribution at the center of the measurement band, only a small fraction of the total radiant output falls within the desired measurement band.

In accordance with the present invention, the emitter surface (and the consequent surface spectrum) is shaped and textured so that the blackbody curve helps to define a band emitter. By suppressing out-of-band emission, this allows an instrument designer to trade out-of-band photons (noise) for in-band photons (signal.) This is effected with a highly reflecting surface having an array of absorbing cavities thereon. The size, shape, and spacing of these cavities are established to absorb at a pre-selected resonance wavelength. As determined from incoherent scattering theory, the size of these cavities is preferably about 1/2p for the desired wavelength. For wavelengths in the MWIR and/or LWIR gas bands, these sizes are well within the limits of current microlithography and microfabrication techniques.

The blackbody curve naturally rolls off more steeply on the short wavelength side, so it naturally defines the short wavelength band edge, even if the surface emissivity does not exhibit a sharp short wavelength cut-off.

Spectral Control

The small surface texture features which make the infrared source of the invention work are preferably made by a random seed texturing process. These features make the surface a selective emitter with full blackbody-like emissivity at short wavelengths but little or no emissivity at longer wavelengths.

Spectral selection is determined using random textured infrared emitters for gas detector applications. A non-blackbody, narrow-band radiator replaces the function of a traditional interference filter and dramatically improves the efficiency of the surface as an in-band emitter. By building a surface which is dark (high emissivity) in-band, and shiny (low emissivity) outside that band, the ratio of usable bandpass flux-to-total flux maximized, and therefore maximizing instrument sensitivity. Sub-micron scale surface structures control the radiator emission spectrum. In effect, the function of the blackbody radiator surface is combined with the function of the bolometer element, and together with some of the function of a thin film interference filter into a single component.

To achieve device miniaturization, it is important to achieve tight spectral control of the infrared emission. This enables maximum infrared absorption signal with minimum parasitic heating of the neighboring detector element.

Figure 7:
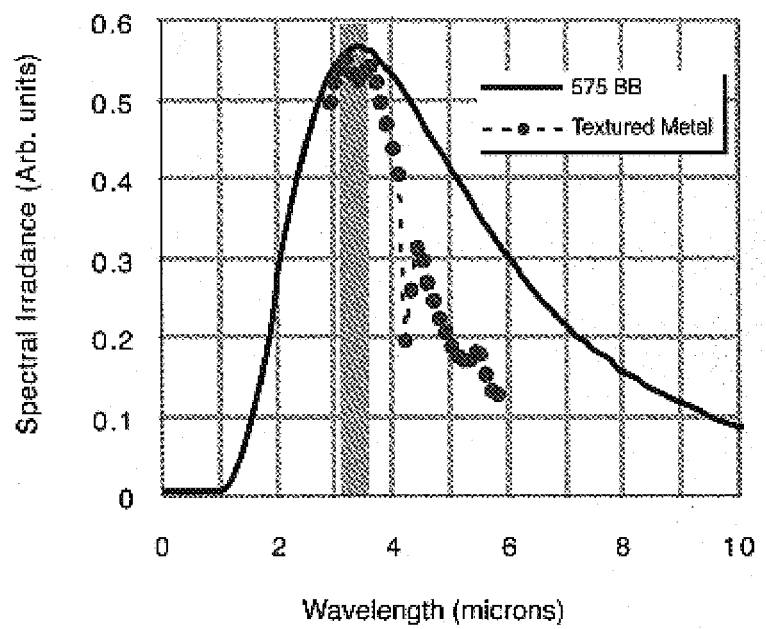
FIG. 7 shows the spectral irradiance as a function of wavelength for a textured metal foil filament of the invention.

The infrared emitters for gas detection are preferably made using random seed texturing of the radiator surfaces. FIG. 7 shows spectral irradiance (relative units) as a function of wavelength for a textured metal foil filament of the invention, as compared with a conventional 575CBB filament. The exemplary metal foil radiator displays spectral narrowing dl/1~0.5 (FWHM), by random texture. A mixture of small and large surface feature sizes accounts for the spectral width. Lithographic techniques are used to produce well controlled surface features for narrow emission waveband.

For an ideal blackbody under these conditions, only a few percent of the total flux is in-band. But the textured metal radiator surfaces suppress long wavelength radiation and therefore improves this ratio. The conversion efficiency of a radiator surface (where neither the surface preparation or the operating temperature were optimized for this purpose) is around 4%. Further improvements can be effected by tuning the spectral emission band specifically for this purpose and carefully maintaining the appropriate operating temperature during the measurement. Preferably, a tuned cavity band emitter with spectral resolution (dl/1) around 0.1, is achieved which is comparable to that achieved with micromesh reflective filters. This level of surface topology (and therefore spectral) control, is achieved using lithographic surface modification techniques.

Figure 7A:
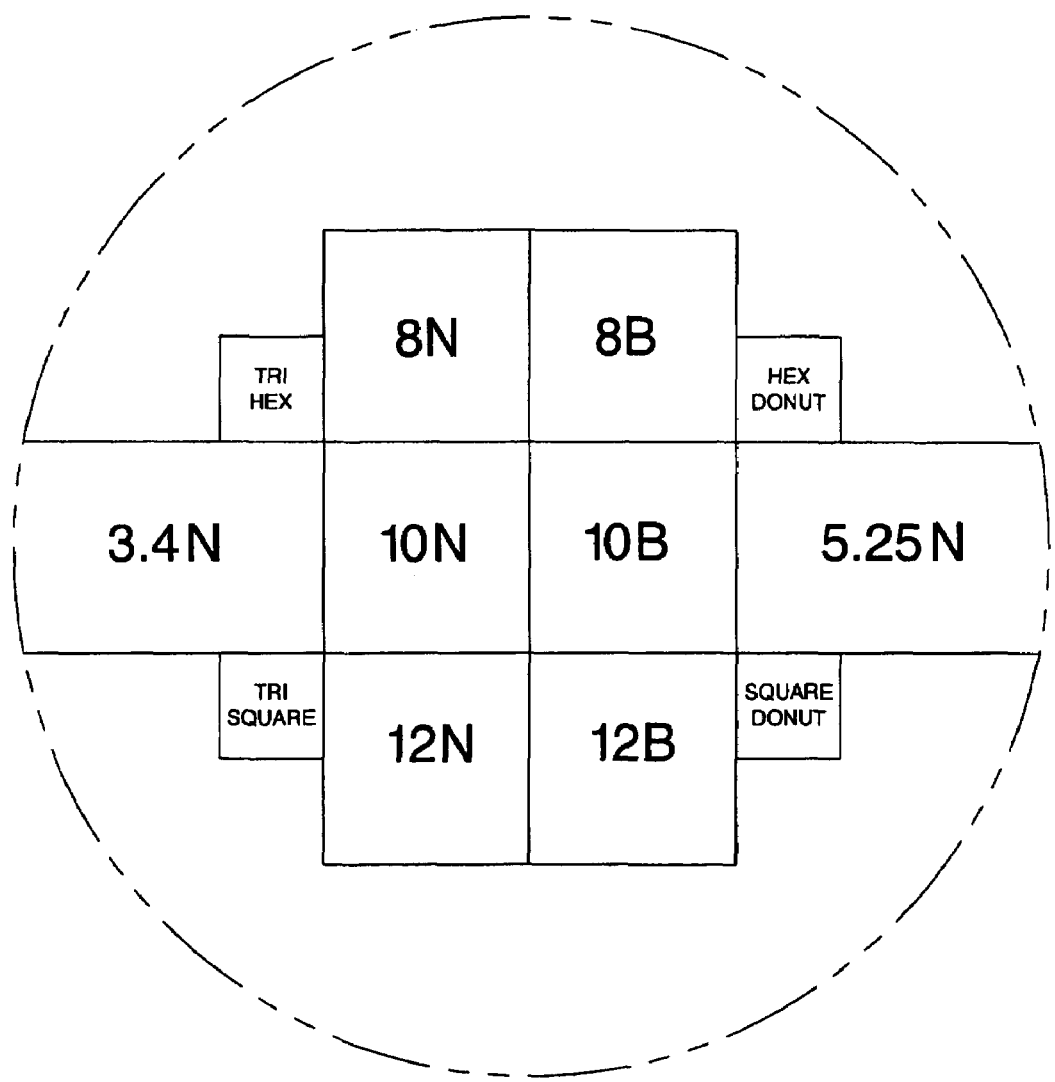
FIGS. 7A(a) and 7A(b) show exemplary mask patterns for an IR source according to the invention.
Figure 7A:
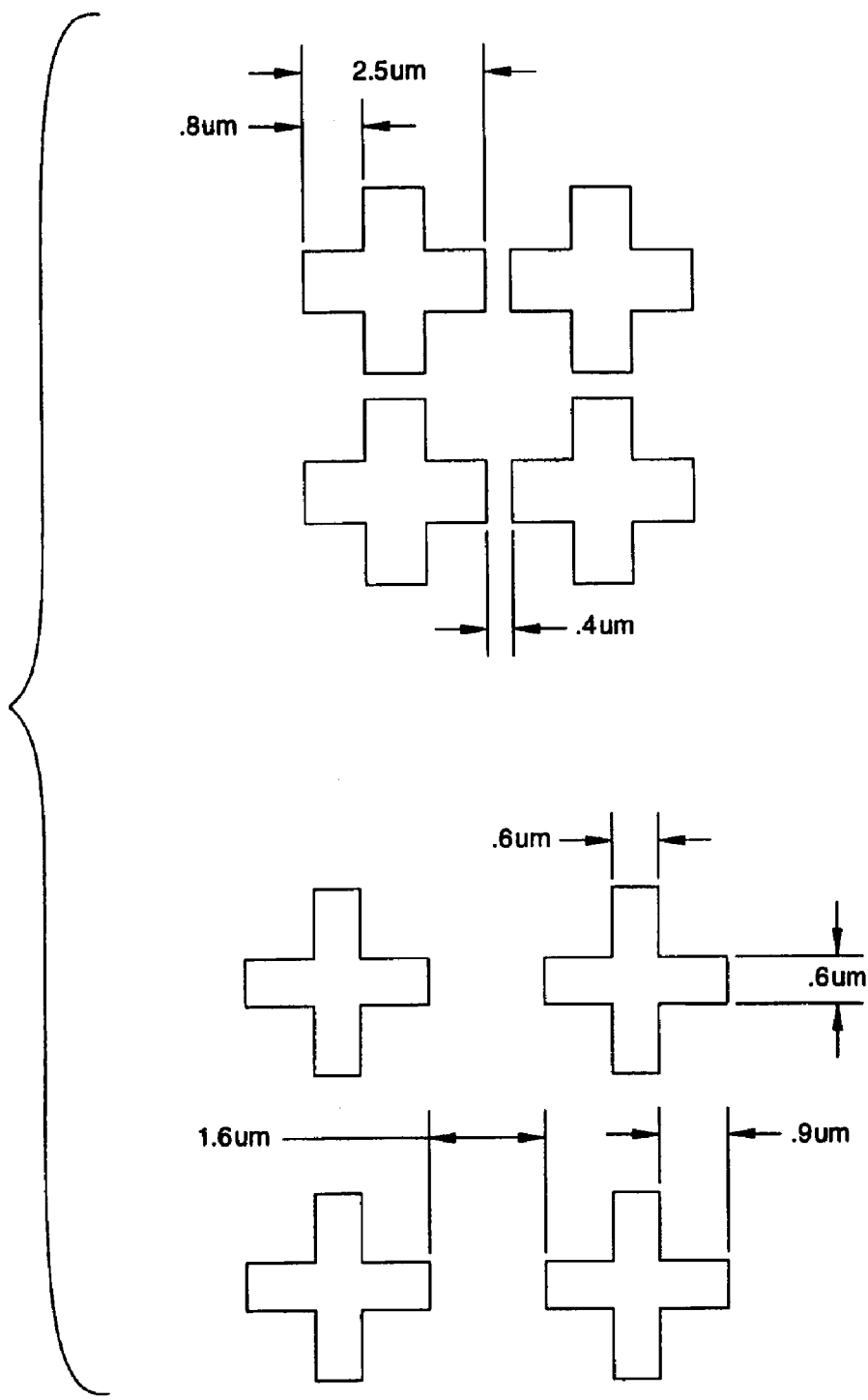
Figure 7A:
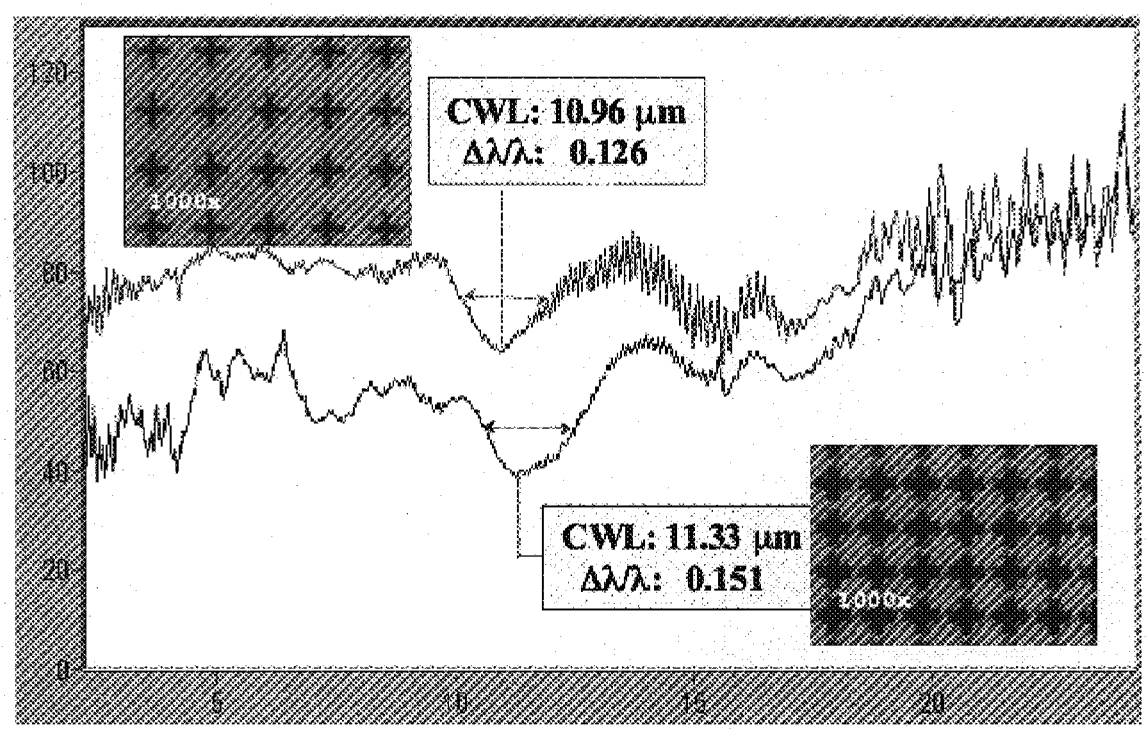

An exemplary emission device is based on the mask pattern shown in FIGS. 7A(a) and 7A(b). The patterns in the center of the mask labeled 8,10 and 12B or N are crosses, either broad (B) or narrow (N) as shown in the detail. Numbering corresponds to the wavelength (i.e., 8, 10, or 12 microns) of the peak absorption. Other patterns can be annular rings and tripoles. The patterns are etched into polished silicon wafers, 1–3, μm deep. A thin layer of aluminum may be evaporated onto the surface of a wafer to change the background emissivity from that of silicon ($\epsilon$=0.7) to that of aluminum ($\epsilon$=0.1).

Figure 8A:
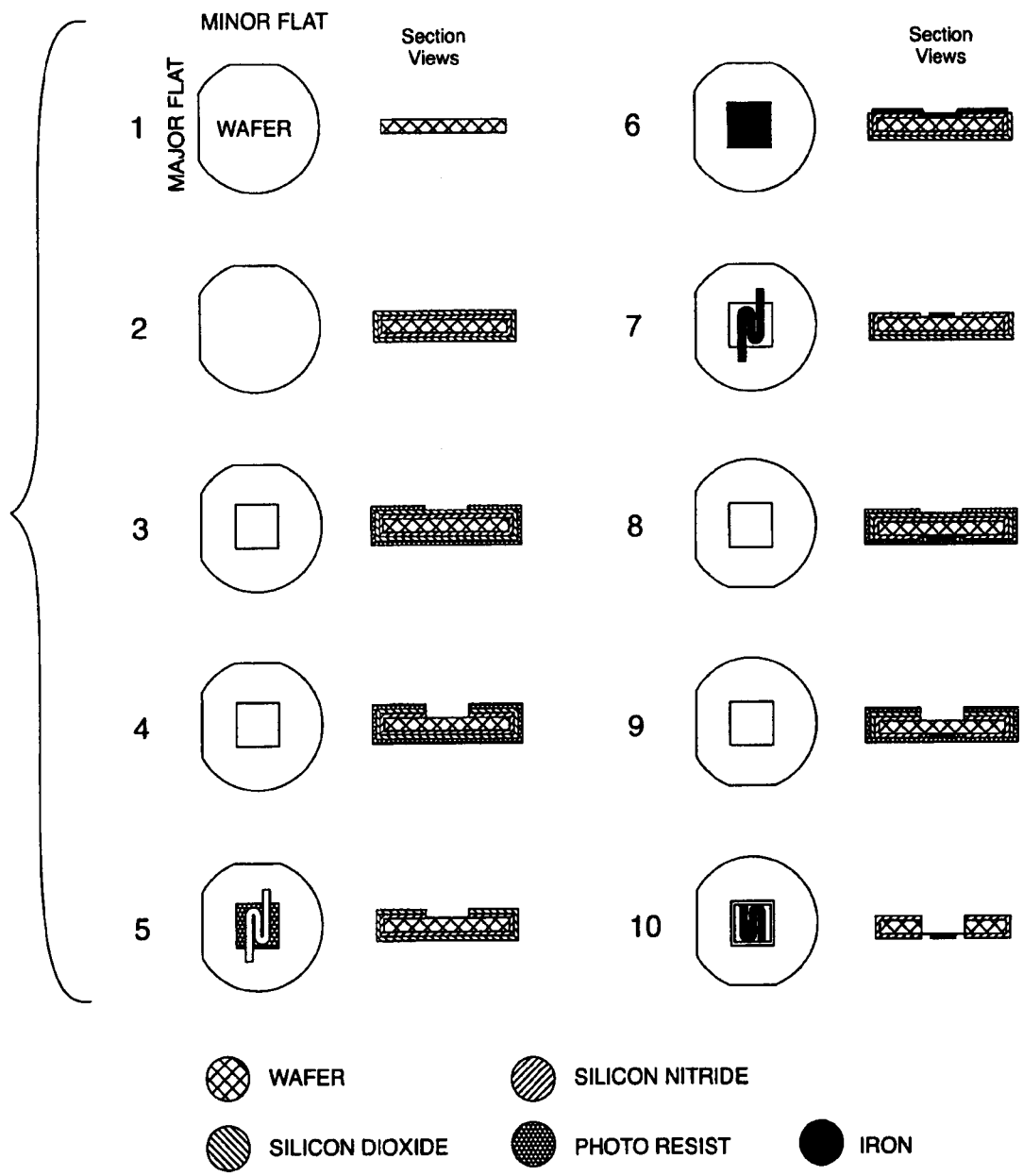
FIG. 8A of sheet 8/17 of WO 00/07411, and FIG. 8B(a)–8B(c) illustrate exemplary window frame construction steps for forming individual radiator elements on a silicon die in accordance with the invention.

The reflection spectra from the exemplary patterned silicon wafer (without an aluminum coating) are shown in FIG. 8A(c). The absorption peaks are consistently shorter than the target wavelengths (by about 20%) and depend on the feature size as well as the unit cell size (feature spacing).

In FIG. 7A(c) the spectra are shown as a ratio with the reflectance of an untreated silicon area on the same wafer. Two areas (12N and 12B, respectively) of the wafer show spectral absorption features related to the size and spacing of patterns on the wafer surface.

With controllable band emission devices of the invention, thermal emission from photonic bandgap surface structures show distinct peaks with a wavelength proportionally to the geometry of the structure. This permits sensor-on-a-chip configurations, for example, where thermal radiation from a "designed" textured surface can be concentrated into a narrow band with low values of $\Delta\lambda/\lambda$. The sensitivity of the detector approaches theoretical limits.

Figure 7B:
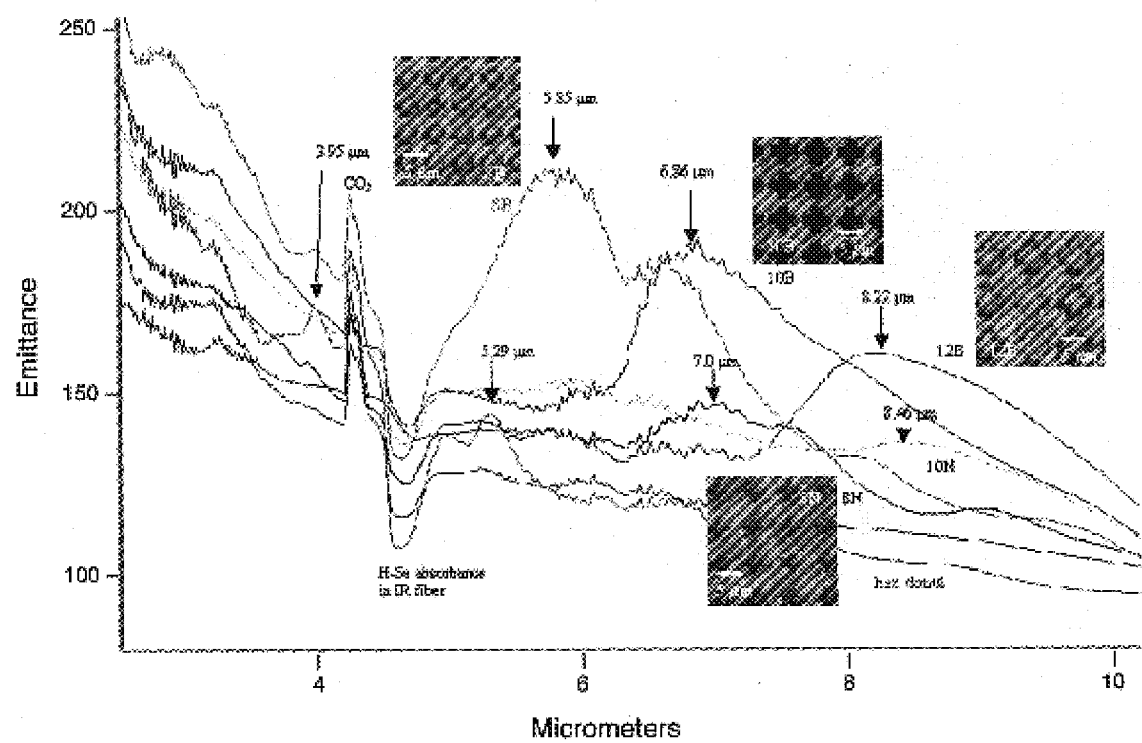
FIGS. 7D(a) and 7D(b) show emission wavelength versus etched cavity size and versus cavity-to cavity spacing, respectively.

FIG. 7B shows emission spectra from aluminized patterned silicon surface heated to 500° C. showing distinct peaks with wavelength varying as geometrical scale factor. In that figure, all sites on the wafer were heated to the same temperature. The surface structure causes sharp emission peaks which appear over a spectral range of nearly an octave. The emission peaks on the aluminum coated wafer have shifted to shorter wavelengths. Various embodiments may use coated wafers, uncoated wafers, and wafers with different doping.

FIG. 7B shows a curve fit to the date from FIG. 7B for a cross design as shown in FIG. 7B. The upper (black) curve illustrates the emission spectrum from an ideal blackbody at 773 K. The lower curve is the semi-empirical thermal model used for estimating instrument signal to noise. It consists of a graybody (with emissivity of 0.48) at a temperature of 773 K, plus excess emission at a peak wavelength of 6.89 microns and an emission width of $\Delta\lambda/\lambda \leq 0.16$. The upper curve in FIG. 7B shows a measured emission data, demonstrating a short wavelength cutoff. Random ion-beam produced texture provides devices with long wavelength cutoff.

Figure 7C:
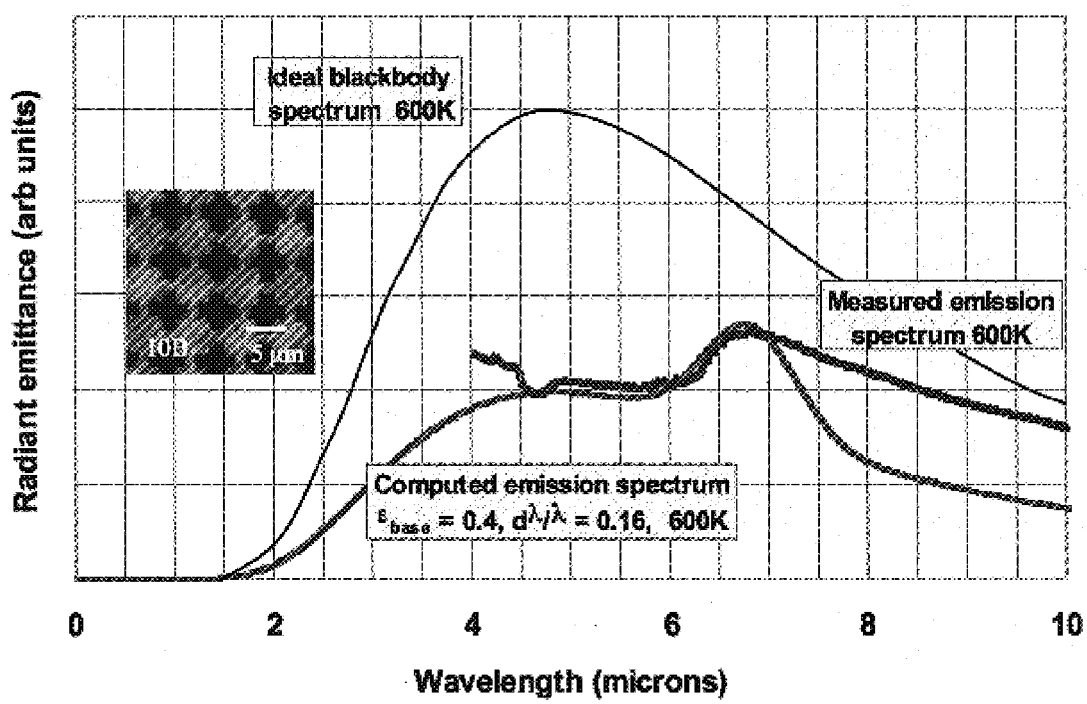

In FIG. 7C, the background blackbody emission from the silicon wafer has a relatively high emissivity of at least 0.48 whereas the emissivity of a good aluminum film is below 0.1. Patterns with a larger fraction of open area (and hence cleaner coatings) show sharper emission peaks.

Figure 7D:
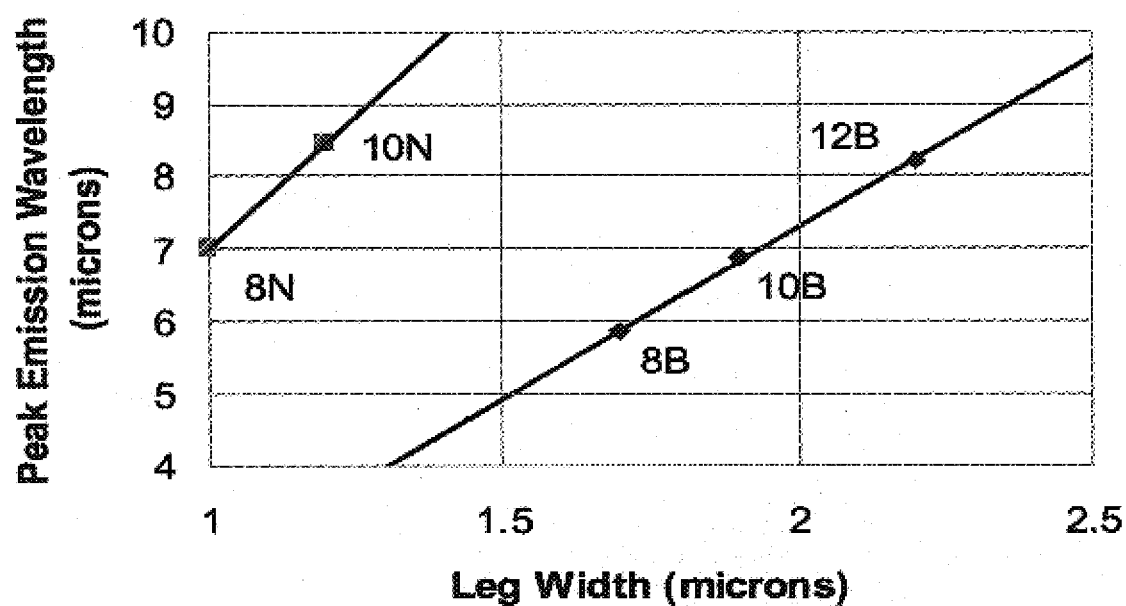
Figure 7D:
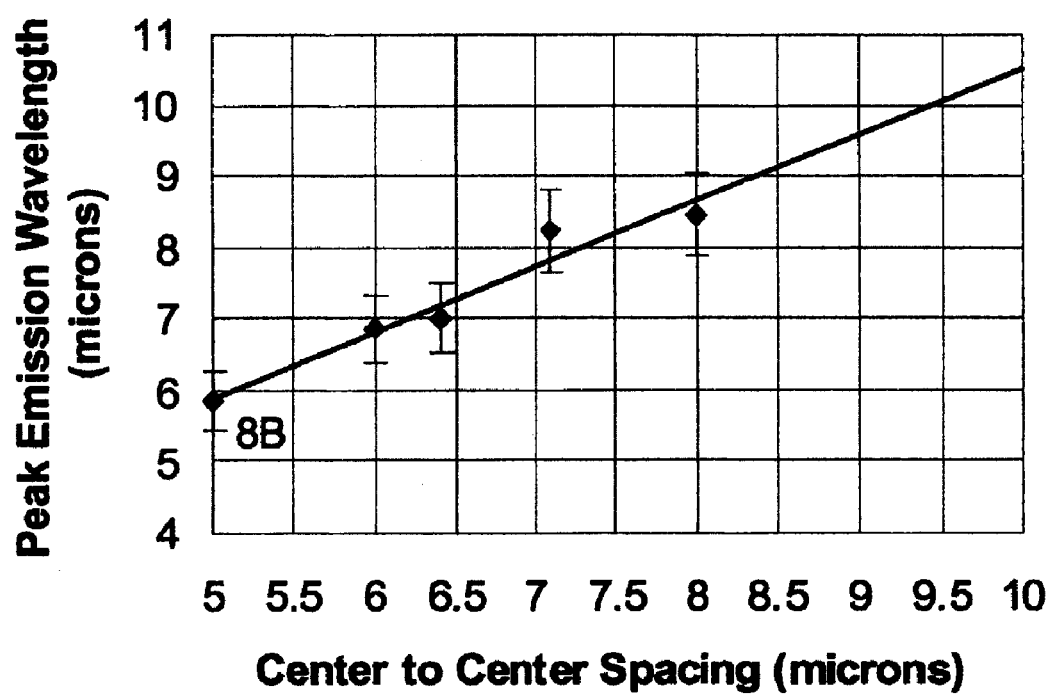

The reflectance and remittance peaks from FIGS. 7B and 7C exhibit a systematic short wavelength-side deviation from their target wavelengths, but demonstrate that PBG peak position and halfwidth are related to size and spacing of the periodic features. FIGS. 7D(a) and 7D(b) show emission wavelength versus etched cavity size (measured as width of cross' leg) and versus cavity-to-cavity spacing. For a 4.65 μm emitter, the cross' leg is about 1.45 μm wide with center-to-center spacing of about 4 μm.

IC Compatible Fabrication

Substantially regular patterns on thin foils are formed by plating or depositing metal films. In one form, a silicon substrate is used as a mechanical support for the foil during subsequent processing.

Subtractive processes based on deliberate, lithographic seed island formation are used with ion beam surface texturing processes. Lithographic masking and exposure schemes are used to achieve the required patterning. Typical lead solder glass materials, used for fabrication of thick film circuits, have a low sputter removal rate, and they are screen printed and chemically removed after processing. Diamond-like carbon films, deposited by chemical vapor deposition, have extremely low removal rates but are not easily patterned. Typical layer thicknesses of the solder glass are a few thousandths of an inch (50–100 mm) and this is comparable to the resolution achievable with screen printing equipment. Conventional microlithography for electronics can produce lines and spaces at least an order of magnitude smaller (two orders of magnitude for state-of-the-art VLSI processes) although the ability to faithfully transfer a pattern to the metal foil is somewhat limited by the thickness of the mask layer. Since the typical size of the pillars which comprise the surface texture is around a micron, micron scale antenna replication is used.

The following method places a regular array of micron-scale structures of a refractory metal oxide on the surface of high TCR self-supporting metal foils. The resultant structure has a surface which is a selective infrared absorber in itself or alternatively, is an improved starting material for texturing using ion milling techniques. The steps listed are conventional photolithographic procedures.

Thin metal foils are deposited on silicon wafers for process compatibility and ease of downstream handling.

Alternatively, self-supporting silicon microbridges are used as the individual emitter elements.

After appropriate cleaning of support disc and foil, the drilled/milled area of the disc is coated with a film of positive photoresist, for example, applied with a clean brush, and the foil is placed over the holes and pressed or rolled into good contact with the disc. Effectively, the holes in the disc are covered, the disc is then held down on a vacuum chuck for the next step.

Positive photoresist is next applied to the entire disc, using a conventional spinner followed by a conventional soft-bake step. The ramp rate up to baking temperature is maintained to be relatively low to allow solvent in the resist layer which bonds the foil to the disc to be released slowly and thus avoid lifting the foil from the disc. A resist formulation designed for use with reflective substrates is useful for this step.

Masking, exposure, and development of the top layer of photoresist is performed in a conventional manner. Clear areas in the mask are positive images of the features to appear on the foil. The hard-bake phase drives off solvents to make the resist film vacuum-worthy.

In cases where a plasma cleaning step is not possible in the equipment used for film deposition, the assembly is then given a short exposure to an oxygen plasma in apparatus for ashing photoresist. The objective is insuring adhesion of the deposited film. Deposition of a refractory oxide film is next done by laser deposition, which allows maintenance of low substrate temperatures. The refractory film covers the entire disc/foil assembly, contacting and, preferably adhering to the foil through the openings in the photoresist.

In the next step, the coated disc/foil assembly is soaked in acetone (or photoresist stripper), in some cases with gentle ultrasonic vibration, to complete the lift-off of photoresist and overlying refractory film and free the foil from the supporting disc. After separation from the support disc, the foil is then cleaned and used "as is", or mounted in an ion mill for texturing as a self-seeded material.

Figure 8B:
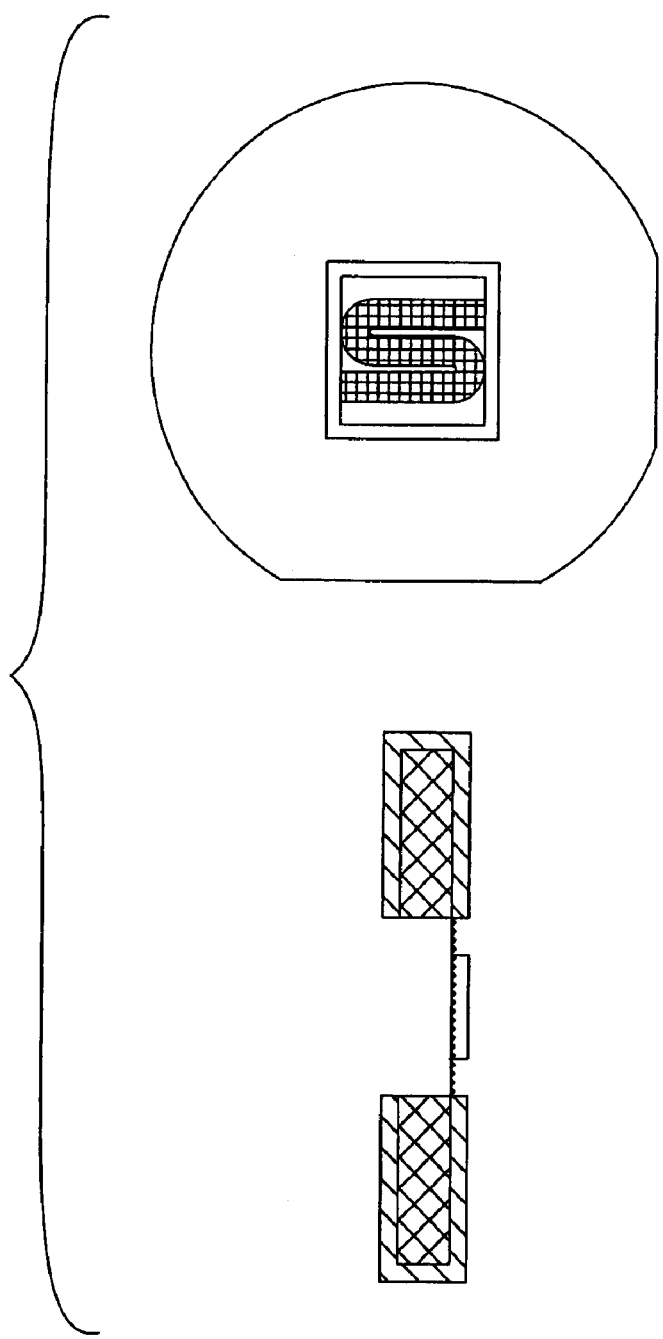
Figure 8B:
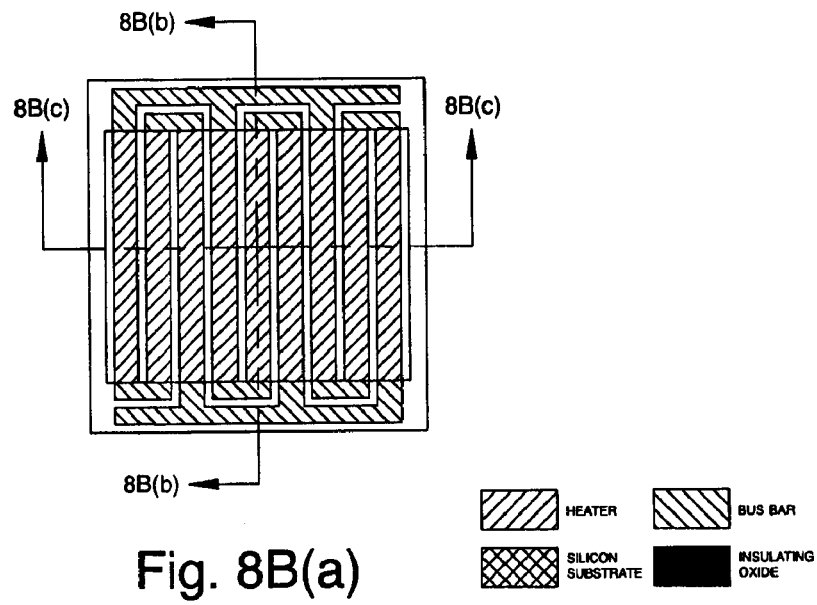
Figure 8B:
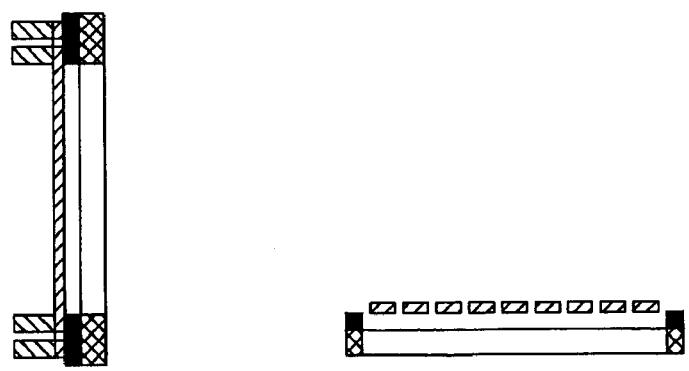

The most desirable packaging alternative is to leave the metal foil intact on the silicon wafer. However, in some forms of the invention, the radiator elements are heated electrically for ready measurement of input power and conversion efficiency. In order to achieve this, the radiator elements are thermally and electrically isolated from their surroundings. A "window-frame" pattern of cut-outs in the silicon substrate is used so that the actual radiator elements are suspended on the remaining silicon, as shown in FIGS. 8A and 8B(a)–8B(c).

FIGS. 8A (ten steps, 1–10) and 8B(a)–8B(c) show the basic window-frame construction technique for forming individual radiator elements on a silicon die. Elements are left on the silicon wafer as a support during microtexturing and then silicon via's are etched from underneath to produce suspended radiator elements.

Integrated Source and Drive/Stabilization Electronics

Wavelength Selective Bolometer Surface

Computer modeling is used to determine the optimum surface shape for desired emission characteristics, based in part on transmission through conductive screen and dielectric-mounted mask arrays. In such models, an incoming electromagnetic wave is considered to produce surface excitations (plasmons) in the metallic screen or grid, and this in turn produces the transmitted wave. The plasmons are considered to be excited directly in order to produce a wave emitted from a surface which has the desired frequency band filter behavior.

Figure 9A:
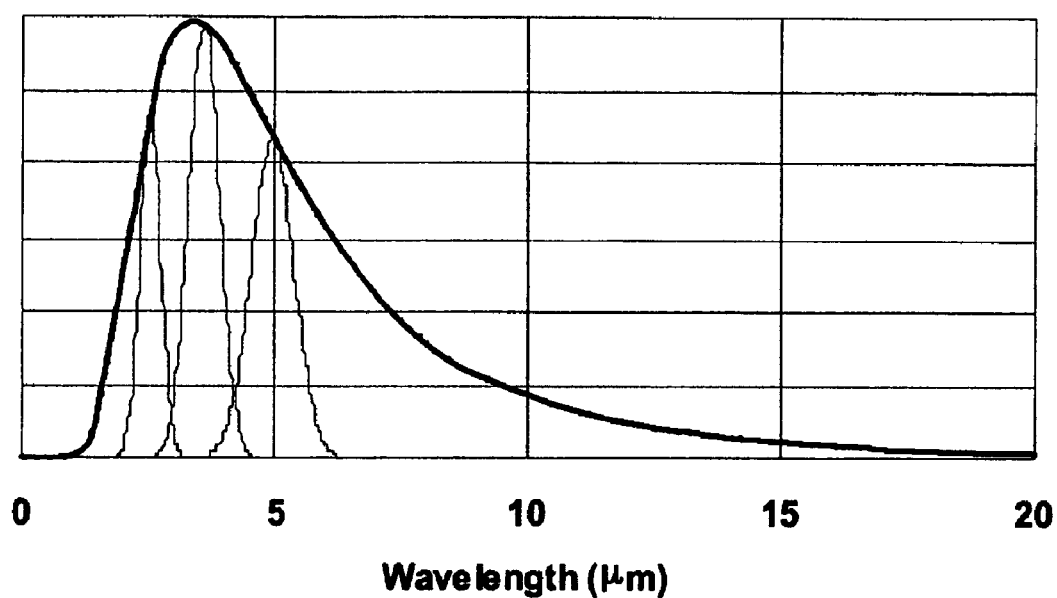
FIGS. 9A and 9B show conversion efficiency gains using lithographic feature design and fabrication according to the invention.
Figure 9B:
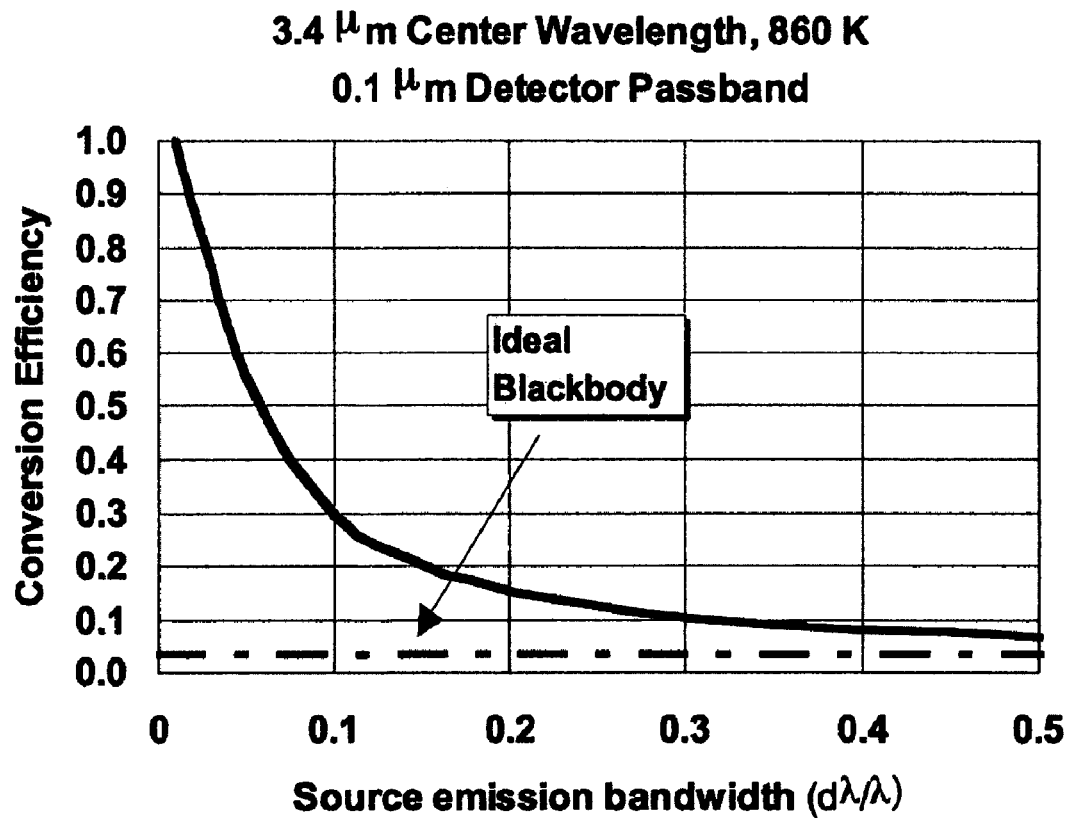

FIGS. 9A and 9B show the conversion efficiency gains using lithographic feature design and fabrication. Such IR sources illustrate a spectral narrowing of 0.5, which gives them almost a factor of four efficiency advantage over an ideal blackbody. By bringing emission width to 0.1 (FIG. 9A), the width achieved to date for filter transmission width, another factor of 4–5× in conversion efficiency is obtained (FIG. 9B).

The size and shape of the repetitive surface feature control the details of the emission spectrum: the peak frequency in the transmission band; the width of the transmission band; the location of the minima which define the band; the steepness of the intensity falloff.

A two-dimensional array with 90° rotation symmetry serves to minimize polarization dependence of the effect, and variation of the details of the repetitive feature (replace a square unit mask by a plus-sign shape, e.g.) enhances desired spectral characteristics. The resonant frequency of the transmitted wave scales linearly with the length of the unit cell in the grid, as expected by analogy with grating studies. Other details depend sensitively upon feature shape (as mentioned previously), the width of lines which create the feature, and feature-to-feature variations. Other features of a textured surface—height of surface features, wall profile shape have an effect, as well.

Existing theoretical studies on transmission properties use models and analogs for prediction. Scalar diffraction theory has been used, as well as a transmission line analog: both with reasonable success. The drawback of such models is that their applicability to a particular situation can only be certified by experimental tests. A priori determination of a region of applicability of particular models is not assured.

In accordance with the invention, transmission line analogs comprise the models for prediction of emission from grids and periodic masks. In these models, each element (unit cell) of the grid is modeled as a simple circuit consisting of a resistance, capacitance and inductance whose values are adjusted so that circuit current matches output field strength of the unit cell. A grid then consists of a large number of identical circuits coupled together with capacitors (for capacitive grids, consisting of conducting elements out of contact with one another) or inductors (for inductive grids, consisting of continuous conductors as in a wire mesh.) The collection of connected circuits implies an output current which are solved by techniques common in transmission line analysis. Analyses such as these are used in calculating transmission properties of grids and masks.

A first principle approach, using Maxwell's equations, is used to establish the validity of this model, and to determine the appropriate R, C, and L values for a given unit element size and shape. The coupling values are similarly found. Once the model has been shown valid for the frequency range of interest, the model is used to simplify analysis of the complete grid. When variation in the unit cell parameters is to be investigated, the analysis becomes more complicated, and the results are cast into a matrix inversion problem where standard computer techniques are employed.

Maxwell's Equations are used as a basis to predict the surface emission, and polarization independence, and then to calculate the emission spectrum of the unit surface cell. Assuming 90 degree rotation symmetry and an infinite grid size, this result is expanded to represent emission from a large surface. Then, small square grids (10×10 features, for example) with random feature-to-feature variation are modeled to determine a representation of the effects of fabrication artifacts and variations.

Integrated Circuit Sensor

Pitch/Catch Source and Detector on the Same Die

The invention further includes a turbulence-based infrared hydrocarbon leak detector which is radically simpler than conventional infrared absorption instruments. Two aspects make this possible. First, a simple structured IR instrument is configured by building a tuned infrared source and conventional infrared detector into a single package. Second, digital signal processing techniques are used to overcome the DC and low frequency drift which characterizes most nondispersive infrared measurements. The sensor does not provide an absolute concentration measurement for hydrocarbons but it is particularly sensitive to the high frequency "noise" caused by the turbulence accompanying changes in local gas concentration. This provides a robust leak detection capability for gases which are not normally present in the sampling environment. Combined with a simple reflector plate to define the gas sampling region, this sensor provides a rugged, reliable, field- and flight-worthy hydrocarbon leak detection capability.

Figure 10:
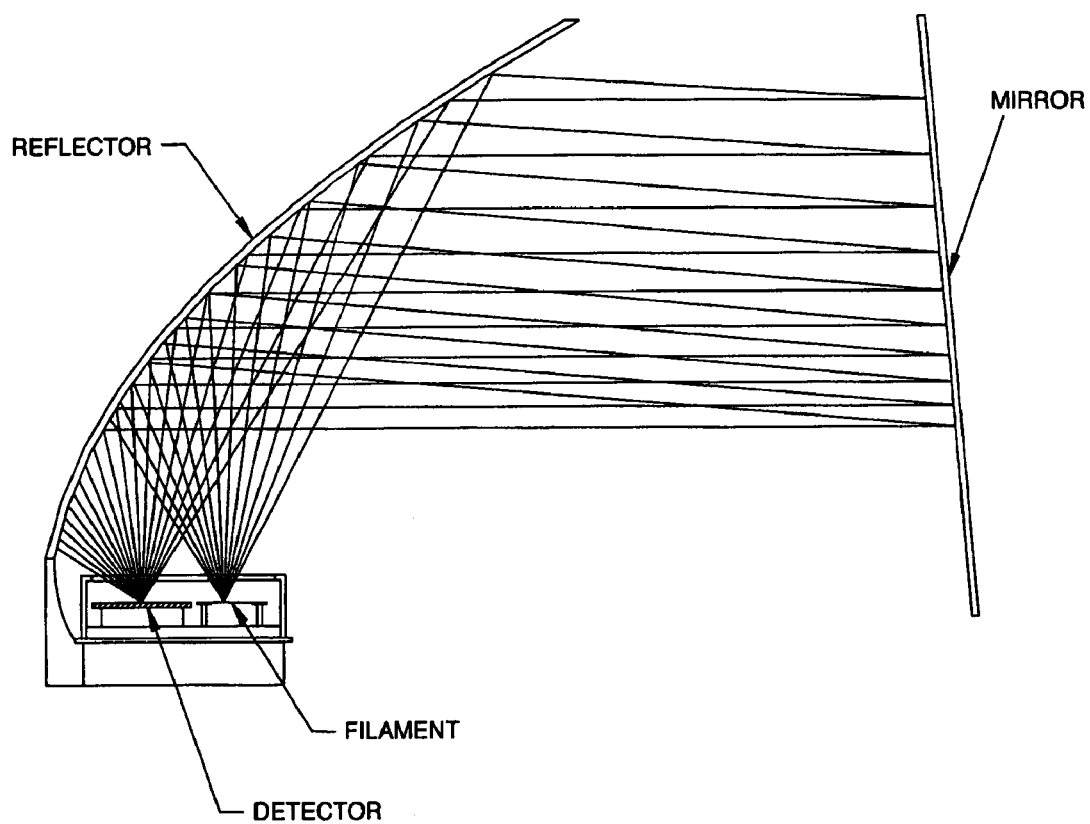
FIG. 10 shows an exemplary IR hydrocarbon leak sensor in accordance with the invention.

FIG. 10 shows a novel, low-cost infrared hydrocarbon leak sensor using an integrated source and detector in an open path atmospheric gas measurement. As a leak detector, the sensor discards low frequency "signal" in favor of the high frequency "noise" associated with changes in local gas concentration. In one form, the entire sensor engine mounts on a TO-8 transistor header.

Hot Bolometer Sensor (With and Without Separate Filter)

An aspect of the invention can be used to form an infrared gas monitoring component to build an integrated on-board exhaust NOx meter. Silicon micromachining technology is used to build a sensor which is radically simpler than conventional infrared absorption instruments. Infrared absorption instruments traditionally contain a source of infrared radiation, a means of spectral selection for the gas under study, an absorption cell with associated gas sample handling and/or conditioning, any necessary optics, a sensitive infrared detector, and associated signal processing electronics. The invention simplifies and reduces the cost of an IR instrument by integrating the function of the infrared source and infrared detector into a single self-supporting thin-film bolometer element. This element is packaged with inexpensive molded plastic optics and a conventional spectral filter to make a transistor-size "sensor engine." Combined with a simple reflector plate to define the gas sampling region, this sensor engine provides a complete gas sensor instrument which is extremely inexpensive and which will approach the sensitivity of conventional infrared absorption instruments.

Figure 11A:
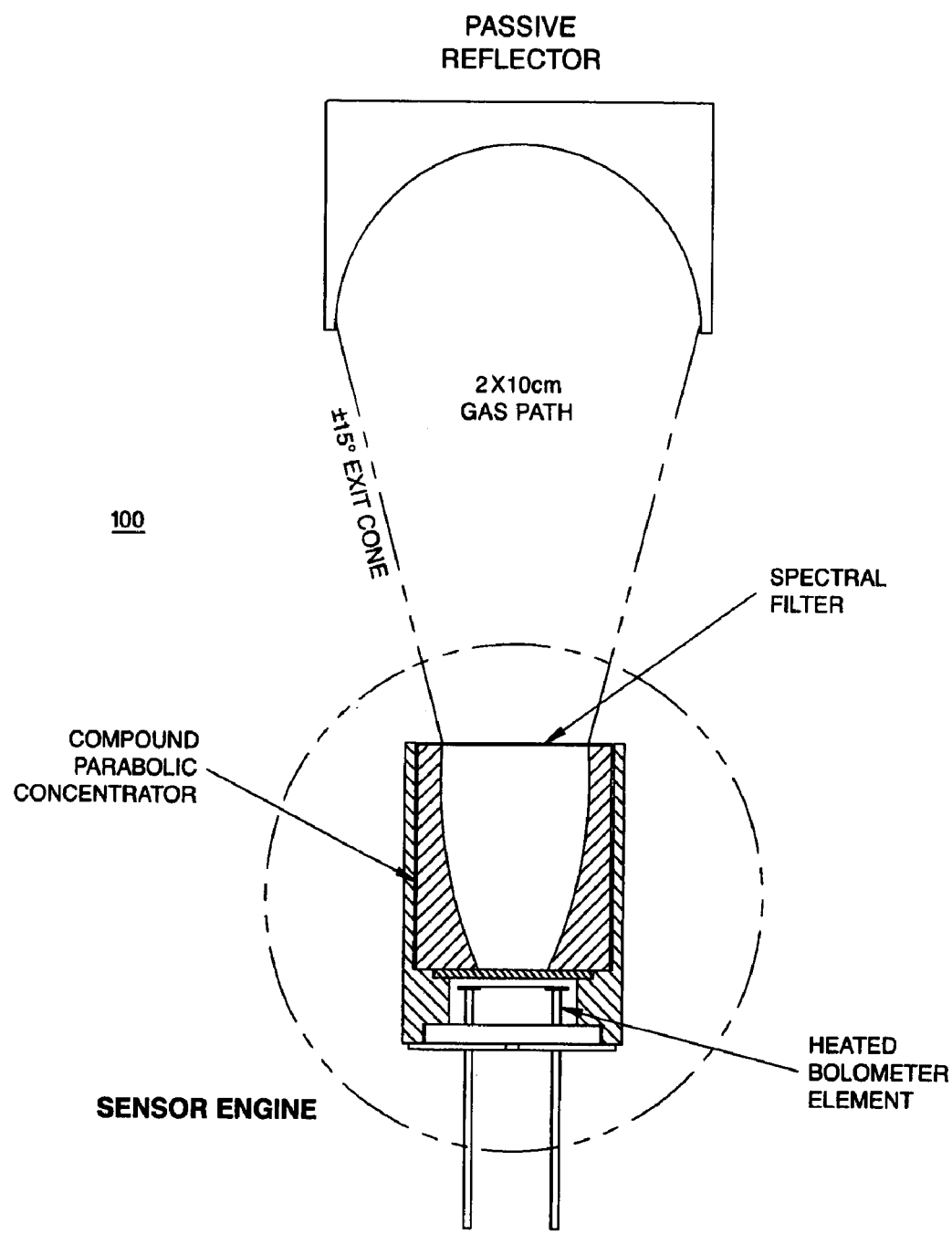
FIGS. 11A and 11B show an exemplary IR gas sensor engine in accordance with the invention.
Figure 11B:
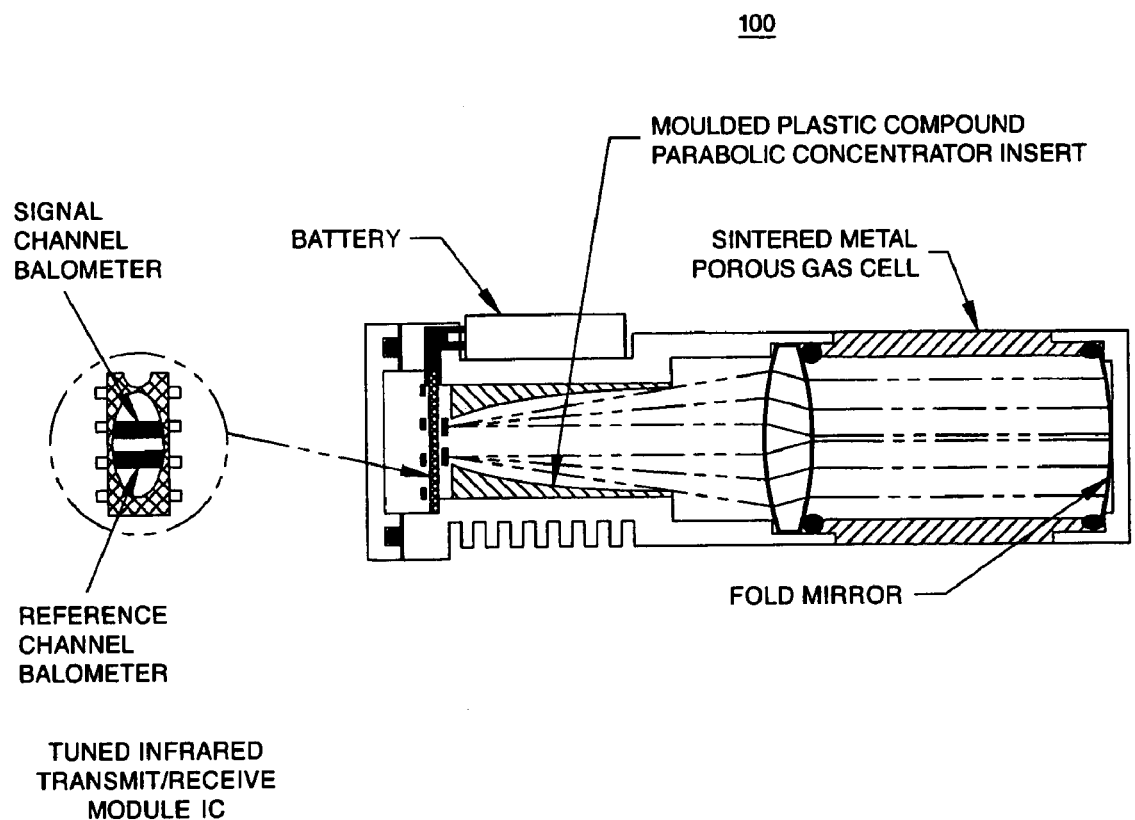

FIG. 11A shows a novel, low-cost infrared gas sensor engine 100 using a heated bolometer element as both source and detector in an open path atmospheric gas measurement. The bolometer element reaches radiative equilibrium with its surroundings at a slightly lower temperature if gas absorption frustrates light re-imaging on the element. The compound parabolic concentrator defines a relatively narrow illumination cone and the passive reflector is designed to provide a pupil-image of the spectral filter onto itself. The entire sensor engine can be mounted on a TO-8 transistor header. FIG. 11B shows a detailed view of the sensor engine 100.

Achieving tight spectral control of the infrared emission is important in making the heated bolometer element work well. The device is particularly effective if the amount of radiation absorbed by gas molecules under study is made measurably large in terms of the overall thermal budget of the bolometer surface. Preferably, a tuned cavity band emitter is constructed with spectral resolution (dl/1) around 0.1, roughly the performance achieved to date with micromesh reflective filters. This raises the conversion efficiency to nearly 15% for the NOx problem. This level of surface topology (and therefore spectral) control, is achieved through micro-electro-mechanical systems (MEMS) technologies.

The embodiments of the sensor engine shown in FIGS. 11A and 11B include a single bolometer which both emits and detects radiation. Those configurations permit construction of devices, such as gas detectors, which are compact and employ a minimum number of component parts. In some instances, however, it is useful to construct such devices with separate radiations sources and sensors. Exemplary devices using separate radiation sources and detectors are shown in FIGS. 11C–11I.

Figure 11C:
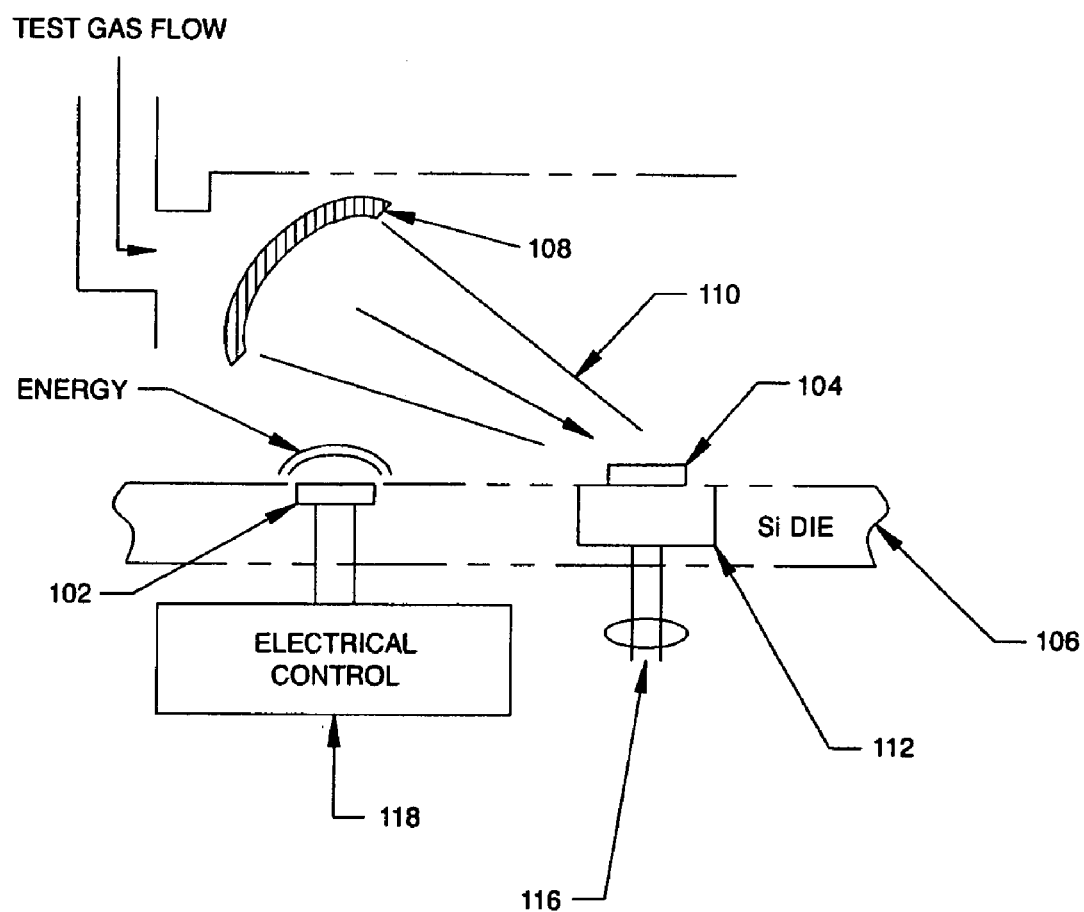
FIGS. 11C–11I show other exemplary devices using separate radiation sources and detectors in accordance with the invention.

In FIG. 11C, radiation source 102 and radiation detector 104 are mounted on a silicon die 106, facing a reflector 108 disposed across a test region 110. The reflector 108 is positioned to effect an optical path between the source 102 and detector 104. The test region 110 is constructed so that an applied test gas flow passes between the source 102/detector 104 pair and the reflector 108, intercepting the optical path. The silicon die 106 includes integrated processing circuitry 112 coupled between the detector 104 and a data output port 116. An electrical control 118 is coupled to source 102 for driving source 102 to emit radiation, preferably infrared radiation with a spectral range including an absorption line of the gas to be detected.

Figure 11D:
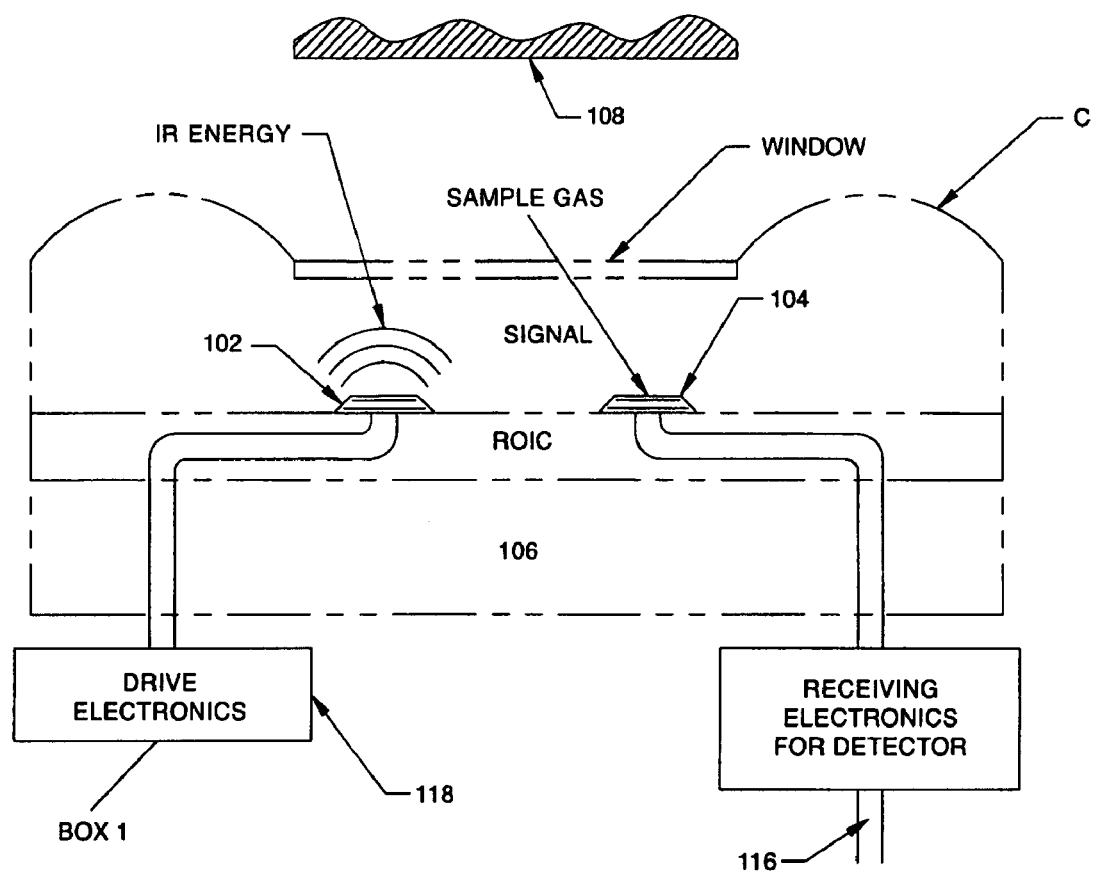

FIG. 11D shows a configuration similar to that in FIG. 11C, but where the source 102 and detector 104 are housed in a closed chamber C, and the reflector (mirror) 108 is external to the chamber C, with the optical path between the source 102/detector 104 and reflector 108 passing through an optically transmissive window W. With this configuration, the gas under test is isolated from the source and detector and any other instrumentation.

Figure 11E:
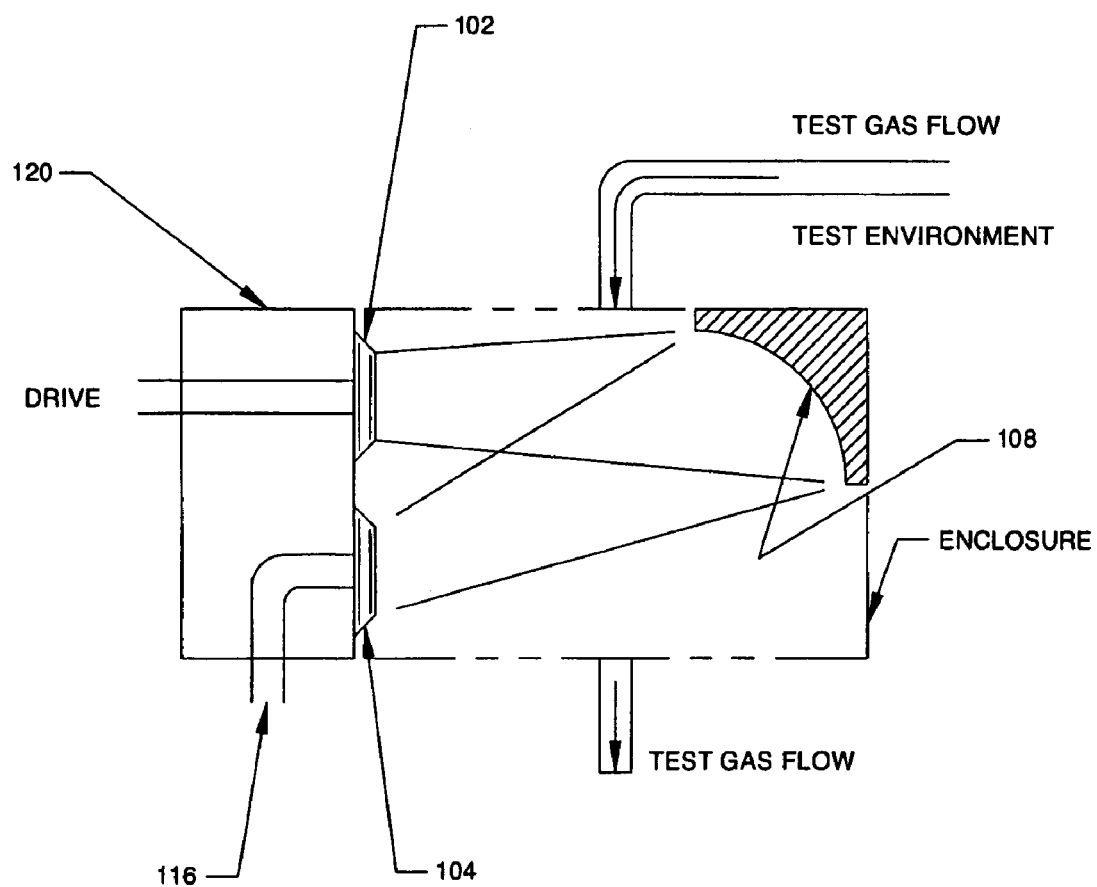

FIG. 11E shows an embodiments similar to that in FIG. 11C, but where the source 102 and detector 104 are mounted within an enclosure E disposed on a single can 120. The enclosure E establishes a test gas flow path therethrough, which intercepts the optical path between source 102/detector 104 and the reflector 108.

Figure 11F:
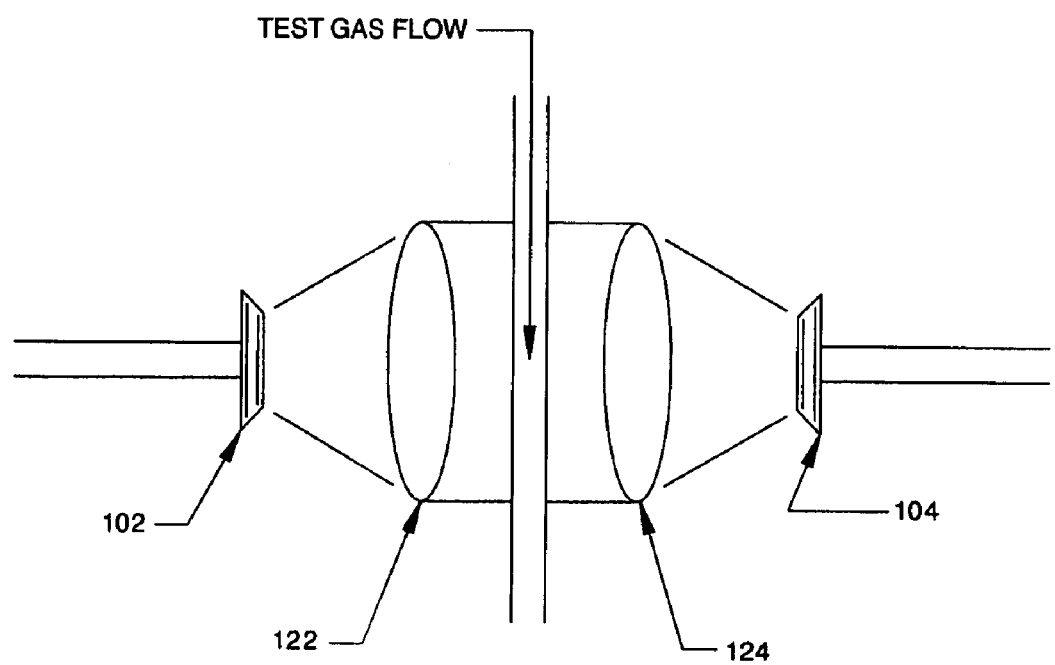

FIG. 11F shows an embodiment wherein a source 102 is disposed opposite to a detector 104, wherein a collimating lens 122 establishes a collimated radiation beam through a test gas flow to a lens 124. Lense 124 focuses the resultant beam onto a detector 104.

Figure 11G:
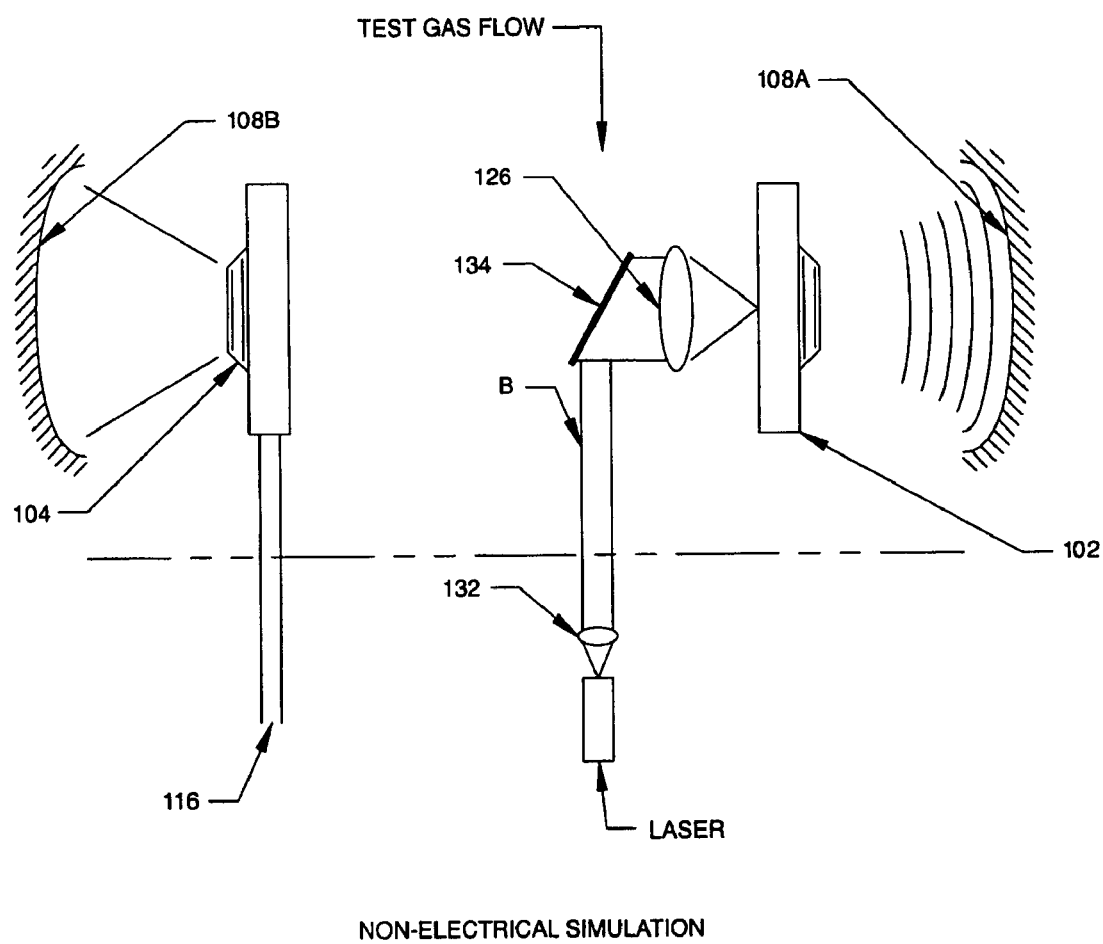

FIG. 11G shows a source 102 which is activated by an optical beam B directed from a high energy laser L (by way of lens 132, reflector 134 and lens 136). The source 102 is back illuminated, so that emitted radiation propagates from an emission surface toward a reflector 108A, which in turn directs that radiation across a test gas flow to a reflector 108B. Reflector 108B focuses the radiation incident thereon to a detector 104 which is coupled to a data output port 116.

Figure 11H:
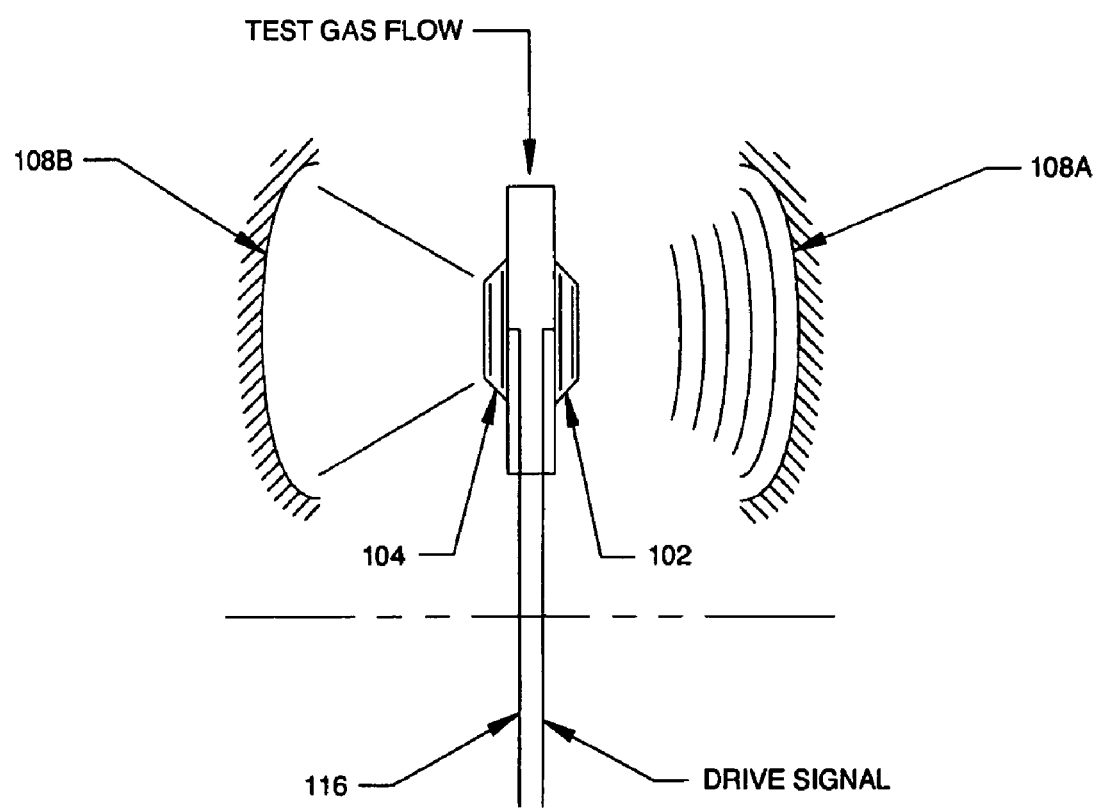

FIG. 11H shows source 102 and detector 104 on opposite sides of a support, each facing a respective one of reflectors 108A and 108B. Source 102 is electrically driven to emit radiation which propagates to reflector 108A. Reflector 108A directs the radiation incident thereon across the test gas flow to reflector 108B. Reflector 108B focuses the radiation incident thereon to the detector 104.

Figure 11I:
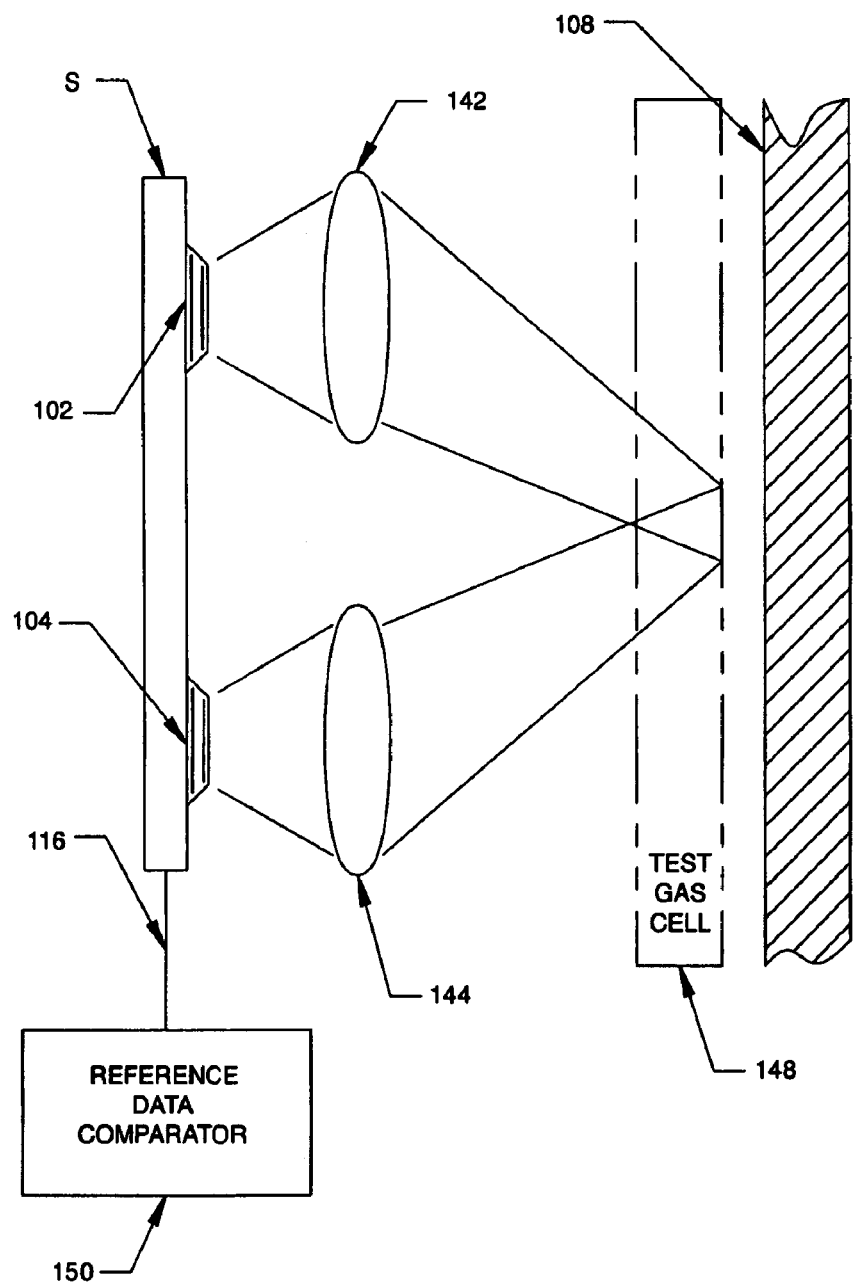

FIG. 11I shows source 102 and detector 104 mounted on the same substrate S, and opposite to a reflector 108. A lens 142 directs radiation from source 102 to reflector 108.

Reflector 108 directs radiation incident thereon to a lens 144, which in turn focuses that radiation onto detector 104. An optically transmissive test gas cell 148 (containing a gas to be identified) is disposed between the lenses 142 and 144 and the reflector 108. Detector 104 provides via data out port 116, a signal to a reference data comparator 150, which compares a received signal (from detector 104) to reference information, for example to permit identification of one or more components in the gas in test gas cell 148.

Wheatstone Bridge Drive Circuit

An individual emitter die is packaged, together with individual infrared detector pixel elements and thin film interference filter windows in TO-8 transistor cans using standard process equipment.

Drive and readout schemes using a microprocessor controlled, temperature-stabilized driver are used to determine resistance from drive current and drive voltage readings. That information shows that incidental resistances (temperature coefficients in leads and packages and shunt resistors, for instance) do not overwhelm the small resistance changes used as a measurement parameter.

A straightforward analog control circuit, the Wheatstone bridge is used to perform that function. It is very simple, very accurate, quite insensitive to power supply variations and relatively insensitive to temperature. The circuit is "resistor" programmable but depends for stability on matching the ratio of resistors. In one form, an adjacent "blind" pixel—an identical bolometer element filtered at some different waveband—is used as the resistor in the other leg of the bridge, allowing compensation for instrument and component temperatures and providing only a difference signal related to infrared absorption in the gas.

An optics test bed is used to evaluate different configurations and perform measurements of the device under benchtop conditions. For elevated ambient (automotive) temperature operation, the device is operated as instrumented tube furnaces and to calibrate the infrared readings against a conventional gas analyzer.

The Wheatstone bridge provides a simple computer interface and since it is implemented with relatively robust analog parts is not susceptible to radiation damage at high altitudes or in space.

Figure 12:
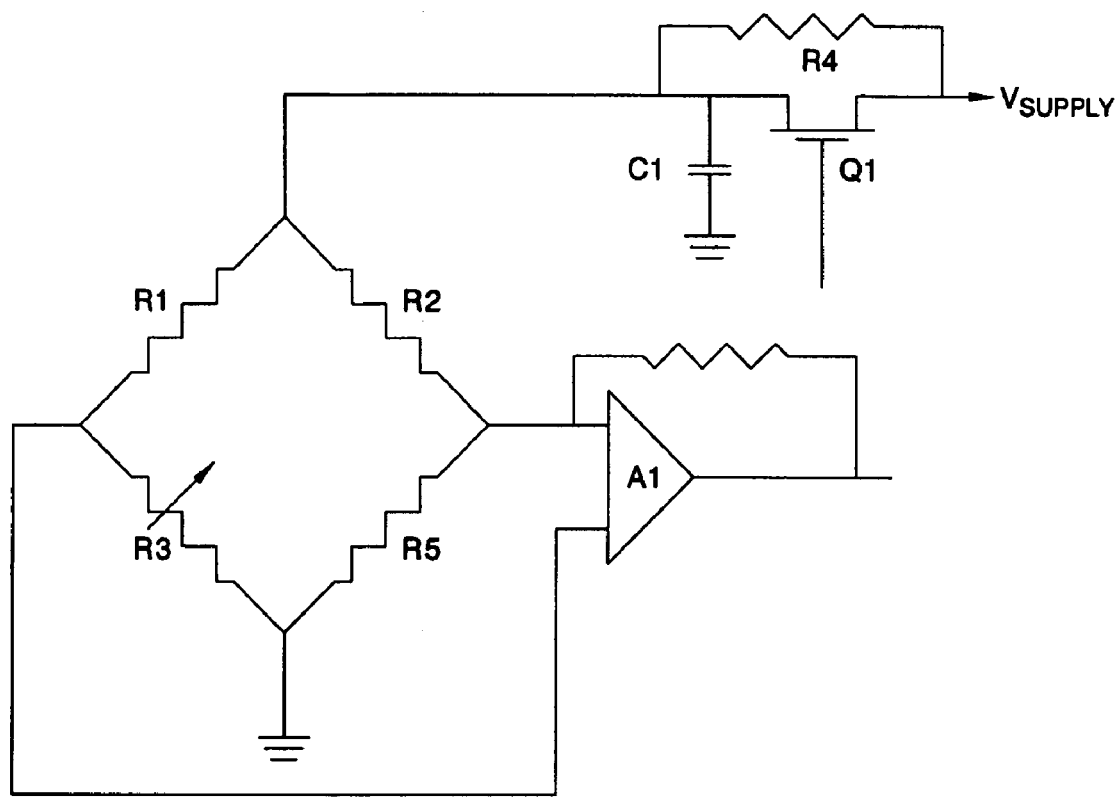
Figure 13:
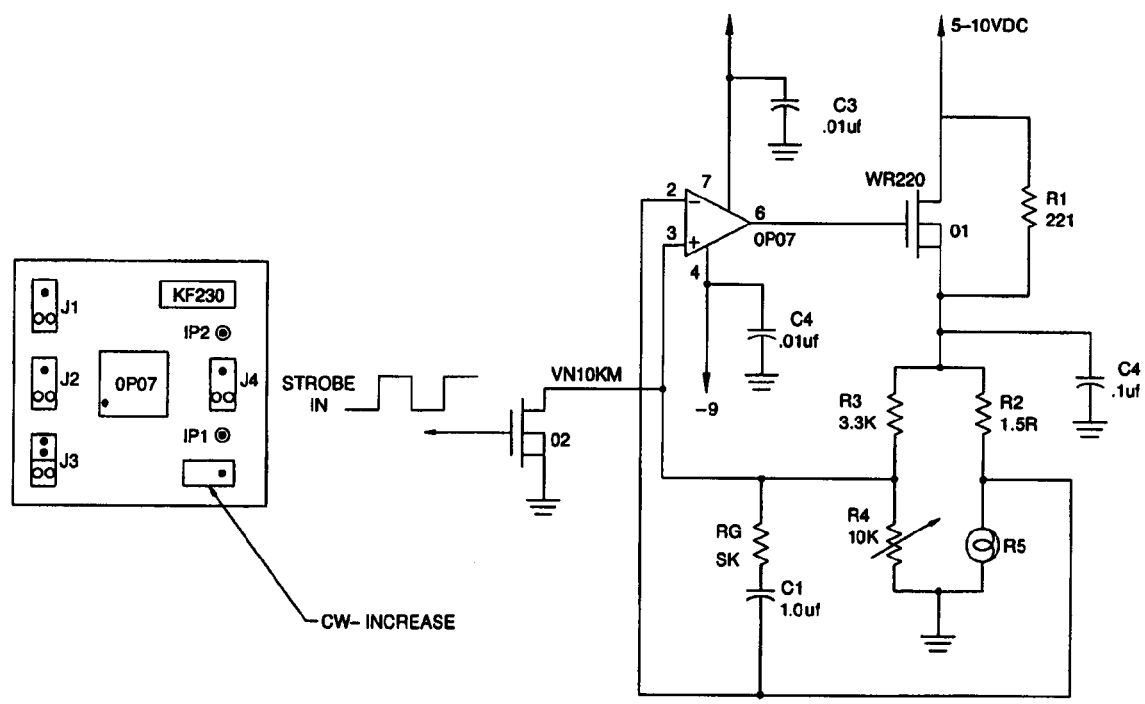
FIG. 13 shows in schematic form, a test configuration for the invention.

For the Wheatstone bridge shown in FIG. 12, bridge is balanced when $R1/R2=R3/R4$, and to first order, temperature coefficients of R1 and R2 can be neglected if resistors are matched. The temperature coefficient of R3 is important but should have negligible effect across delta T caused by the gas absorption. Preferably, the bridge is carefully balanced for the designed operating temperature. The estimated errors from an analog readout of this circuit come from the amplifier input offset and input bias currents which introduce offset voltage or error term. FIG. 13 shows a test configuration.

Turbulence Detection and Signal Processing

In connection with industrial gas sensors, we have found that source-detector-electronics combinations can readily be stabilized to provide signal to noise performance of 1000:1 or better under conditions of stable temperature and steady state gas flow. Typical conditions are pulse frequencies of 1–10 Hz, well matched to the speed of available thermal detectors. However, high frequency transients associated with changes in gas flow provide a significant disruption. Ordinarily, in fact, detector preamplifier circuits are severely filtered to suppress these high frequency transients.

Most detectors have poor low frequency characteristics and are subject to 1/f or low frequency noise and drift. This is also true for most DC amplifiers where precision components are required for good low frequency response. This noise is avoided by selectively filtering and amplifying only those high frequency components present in a turbulent gas stream. In order to separate these high frequency components, a narrow, band pass filter is used; these filters are preferably constructed using low cost integrated circuits.

Emitter elements (narrow spectral band, high cold resistance) are used with filtered pyroelectric detectors. A/D converters are used to collect and analyze the data and optimize the signal processing sequence.

Although the high frequency components are difficult to see in the power spectral density plots, the thermopile detectors used have a poor high frequency response. Lead selenide and pyroelectric detectors have a much better high frequency response than the thermopile detector.

Figure 14A:
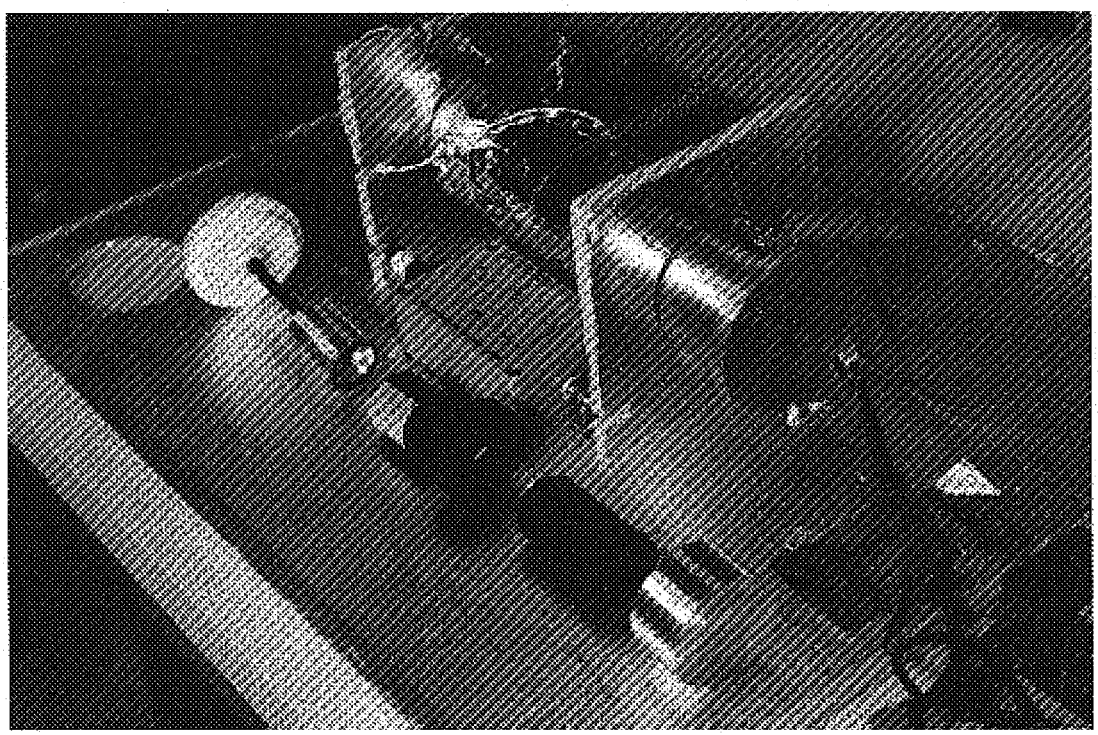
FIG. 14A shows an exemplary nondispersive test bed using the invention.
Figure 14B:
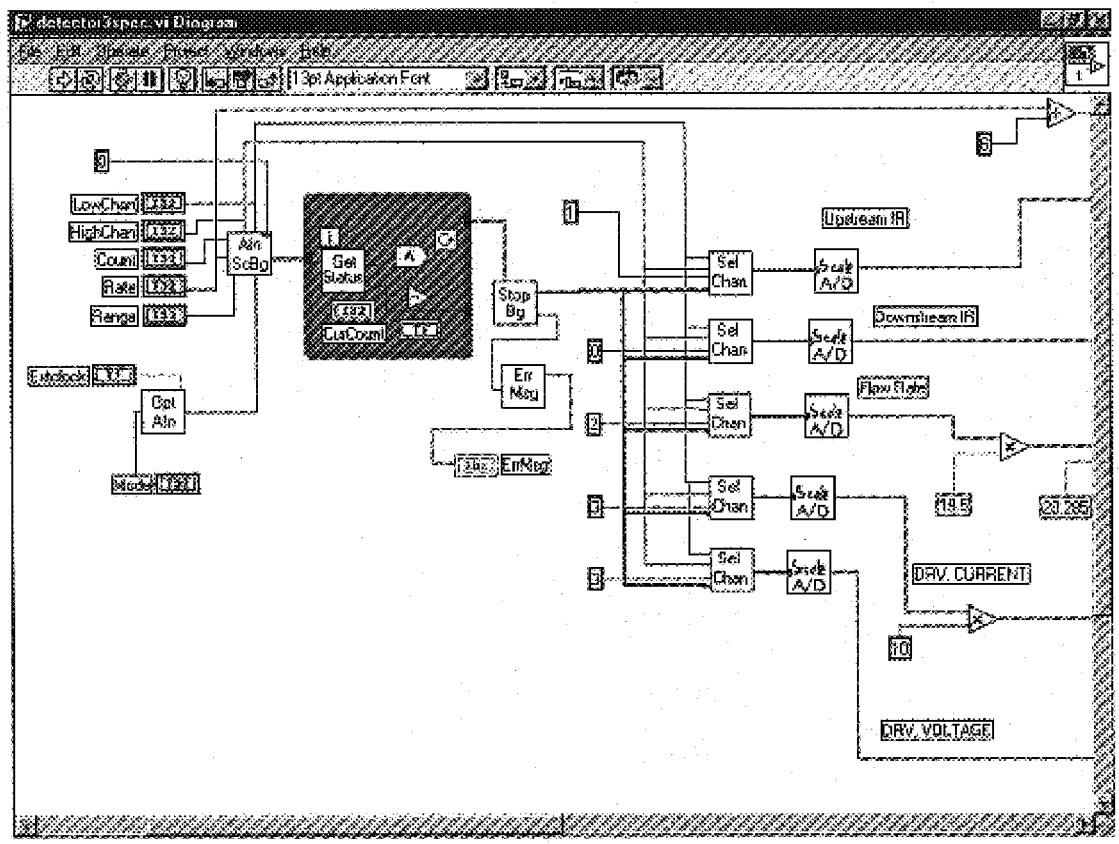
FIG. 14B shows in block diagram form, an exemplary signal processing for date reduction for the test bed of FIG. 14A.

FIG. 14A shows a typical nondispersive infrared gas sensor test bed including infrared radiator and detector, suitable filters, and a small environmental chamber for performing thermal cycle and gas flow tests. FIG. 14B shows a typical signal processing stream for data reduction.

Automated data collection analysis software, or off-line data analysis software is used for signal processing, rapid prototyping of data collection and analysis systems. Real-time power spectral density plots and other signal processing techniques identify and isolate those frequency characteristics, that will enable this simple, yet effective gas detection approach.

Figure 15:
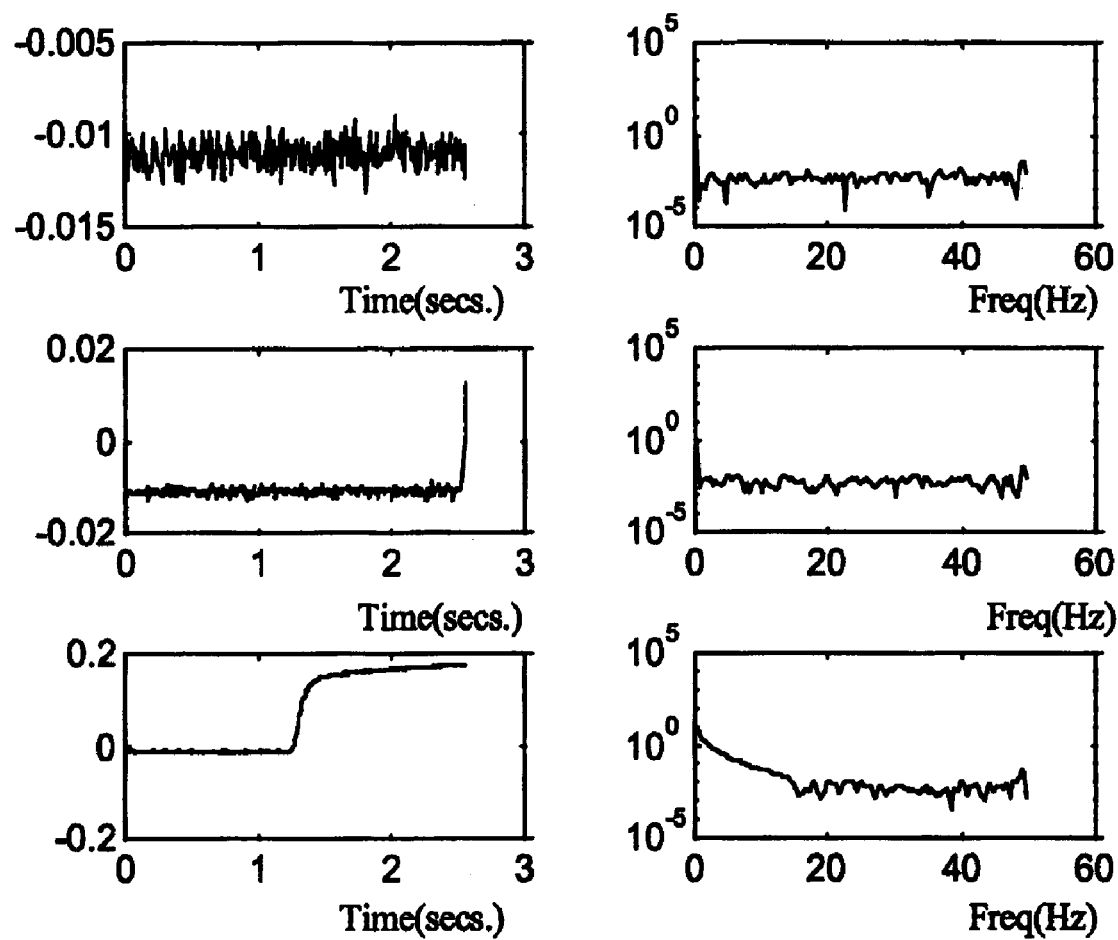
FIG. 15 shows a calibration spectrum for a hyperspectral imaging system of the invention.

FIG. 15 shows measured data from a pulsed-source and thermopile detector combination, illustrating the high (20–40 Hz) ripples associated with changes in gas flow. Long considered a problem for IR gas detectors, this characteristic is used to exploit this "noise" as the primary "signal" for a leak detector.

Multi-Pixel Sources for Scene Generators and FPA Health Check Multi-Pixel Calibrator for Hyperspectral Imagers A tiny, self-referencing band emitter is used for absolute radiometric calibration of infrared spectral channels. This simple, rugged device can be incorporated directly into a radiometric instrument, or into a field test kit. Microelectromechanical (MEMS) fabrication techniques are used to produce a photonic band gap infrared emitter surface with a narrow emission band tuned to the infrared spectral channel under test. A discrete single-channel (less than 1 mm active area) radiometric calibration element is used. This configuration is stable, repeatable, and has high power conversion efficiency and out-of-channel rejection. The configuration can provide a transistor-sized multi-pixel, multi-channel hyperspectral calibration tool.

A simple built-in radiometric and wavelength calibration device is used for hyperspectral imaging systems. A silicon bridge emitter element has a photonic band gap (PBG) surface tuned to emit over a narrow infrared waveband. With very low thermal mass and high temperature coefficient of resistivity (TCR), this element acts as its own thermistor for self-referencing, electronic feedback control.

Figure 16:
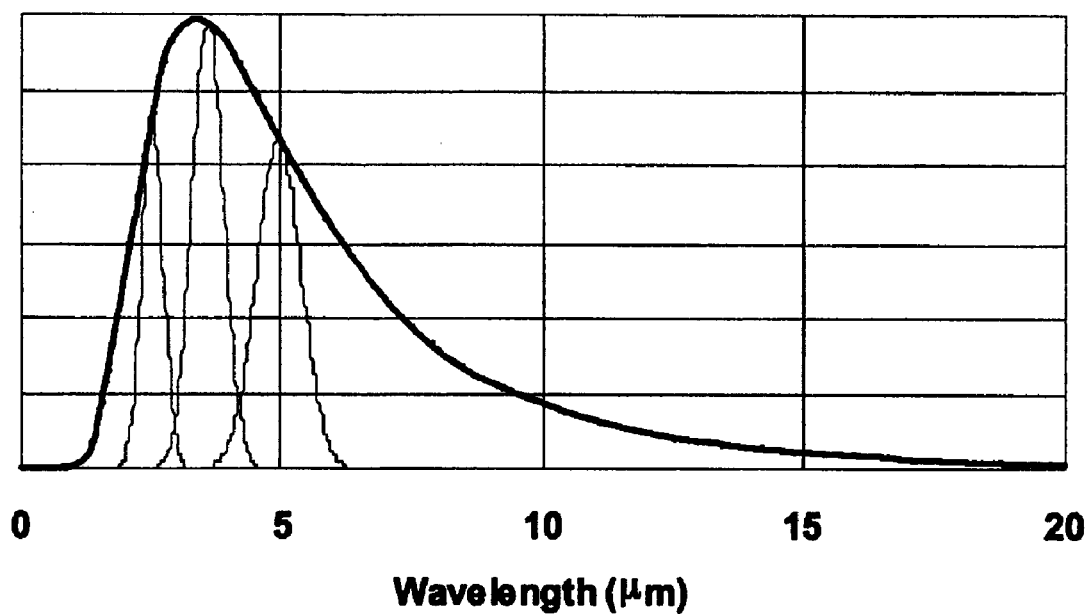
FIG. 16 is duplicative of FIG. 9A.

FIG. 16 shows a simple, built-in calibrator for hyperspectral imaging systems, using silicon micro bridges with a photonic band gap surface structure to achieve narrow band emission and absolute feedback temperature control in the infrared.

Hyperspectral Imaging

Passive infrared spectra contain critical information about chemical make-up while broad-band infrared images provide information on the location, presence, and temperature of objects under observation. Hyperspectral imaging, the ability to gather and process infrared spectral information on each pixel of an image, can ultimately provide two dimensional composition maps of the scene under study and this data is critical for ecosystem inventory and status monitoring. These studies routinely require data in the near- and mid- infrared spectral bands, over large areas, at a reasonably high resolution suited to ecological studies. Data goals include complementary surface moisture and surface (vegetation) temperature data taken in registration with the shorter wavelength data (allowing precise and straightforward correlation with LWIR data) for plant coverage, deforestation, and plant health monitoring studies. Variations in surface albedo within from frame to frame and even within a single frame make it difficult to infer accurate temperature measurements from bandpass flux at a single wavelength. This may be particularly acute for deforestation studies where sudden loss of vegetation coverage would be expected to produce surface humidity changes with simultaneous shifts in surface temperature and surface albedo.

A traditional solution is to measure infrared bandpass flux in adjacent spectral bands to allow extraction of accurate color temperatures. Hyperspectral imaging can provide surface temperature and humidity mapping, at a resolution compatible with the shorter wavelength systems, over inaccessible regions where this data is not available from ground monitoring stations or other sources.

Current hyperspectral imaging systems such as the NASA/JPL Airborne Visible Infrared Imaging Spectrometer (AVIRIS) and Kestrel's Fourier Transform Hyperspectral Imager (FTHSI) are bulky and expensive which renders widespread use of the technology impractical, especially for commercial applications. Rapidly evolving uncooled hyperspectral imaging systems, based on recent advances in infrared focal plane array technology, can provide simultaneous mid-wave (MWIR) and long-wave (LWIR) data for coastal ecology studies. These devices, which must operate under field and flight conditions over large temperature and humidity ranges, require periodic radiometric and spectral calibration to assure long term accuracy.

Radiometric Calibration

Hyperspectral image measurements are difficult to make in the field since the instruments must operate unattended (or with minimal attention) in hostile environments, over extreme field temperature and humidity ranges. Much of the important irradiance information is in the 1–3 mm spectral band where low signal and drift in infrared sources and infrared detectors make stability and calibration difficult. In fact, the standard NIST FAL, T-10 reference bulbs generally used for laboratory calibration have very low signal in this waveband. But the atmospheric research community has made steady progress in the accuracy and reliability of these measurements and there is now a broad consensus on absolute standards for bolometric radiometry established through bi-annual international inter-comparisons between instruments used by various groups and a gold triple point standard. In general terms, the state of the art for absolute accuracy in these measurements has progressed to around 0.3% (3s).

The most effective strategy for maximizing instrument sensitivity is calibration to identify and compensate for gain and offset variations. This is done with conventional blackbody sources which depend upon large size and thermal mass to achieve uniform temperature. These sources are not easily incorporated directly into the instrument. As a consequence, calibration is infrequent and, particularly for instruments stationed at inaccessible locations, very infrequent.

Accordingly, to one aspect of the invention, a miniature, electrically-modulated multispectral line source weighing a few grams and occupying a fraction of a cubic centimeter provides the solution to this problem. The heart of this source is an array of photonic band gap narrow band emitter pixels. Each pixel radiates only within its designated spectral band and achieves temperature stability by heating and cooling on a time scale much faster than thermal diffusion. Its low thermal mass, near-perfect in-band emissivity, and high temperature coefficient of resistivity cause it to precisely follow its drive current, permitting instantaneous feedback and precise temperature control. The source is readily packaged into radiometric instruments where its low power demand permits remote, battery-powered operation under computer control.

The stability of conventional, cavity-style blackbody sources depends on good thermal conductivity (to minimize spatial temperature gradients) and a large thermal inertia (to minimize temporal fluctuations). This determines their weight and power consumption, both of which are typically large. The IR source of this aspect of the invention, because it is based upon a few-micron-thick textured emitter element, does rely on its thermal mass for stability, but instead depends upon a stable electronic drive supply. This is an important advantage for the source of the invention because super-stable, precisely controlled electronics are much easier to engineer than a highly stable thermomechanical system and, when built, respond orders of magnitude more quickly to programmed changes, weigh less, occupy less space, and are less expensive than massive radiators.

Conventional blackbody sources require long lead times for warm-up and stabilization and, during these times, they place a parasitic heat load on components in the optical train. For components at cryogenic temperature, the source-induced heat load is especially burdensome because it is continuous, and heats the optical train even when not in use as a reference or for calibration. Miniature IR sources of the invention, on the other hand, rely upon electrically heated filaments of such low thermal mass that their temperature at all times correlates precisely with the current flowing through them. They can be heated (and cooled) in milliseconds, delivering a current-following temperature profile exactly matching the drive pulse. Because they rely on electrical pulse shaping and current control rather than thermal mass for stability, these miniature sources have several important advantages. First, they need only be powered for a short time when required, thus eliminating parasitic heating. Second, their low thermal mass and high radiant output allow them to achieve a very high temperature-slew-rate with virtually no thermal hysteresis. This means that at any instant, filament output is directly related to electrical drive power. Effectively, this converts the thermal stability problem into a matter of assuring electrical stability.

Portable MTF (Modulation Transfer Function) Tester

According to another aspect of the invention, an infrared resolution tester which is a thermal version of the familiar resolution test patterns for visible band optical systems. Based on the use of miniature textured metal radiators for flat-field correction of flight systems, the invention is based on lithographic techniques to build a postage-stamp sized device with alternating bands of polished (emissivity, $\epsilon \approx 0.01$) and textured ($\epsilon \approx 0.99$) metal to form the familiar USAF 1951 optical resolution test pattern. The integrated resolution tester based on this device is light-weight, low power, and responds rapidly to turn on/turn off commands. This device is mounted on a temperature controlled stage and demonstrates performance with collimating optics. This device is a flightworthy resolution tester for field and flight monitoring of infrared imaging systems.

For any imaging system, one of the most important figures of merit is resolution. This is typically expressed as a modulation transfer function (MTF), or contrast as a function of spatial frequency. For visible-band systems, MTF has historically been measured with standard resolution test charts; because no such devices are available in the infrared, designers typically rely on slits (often home-made) in a metal foil mounted in front of a large cavity-style blackbody to make the measurement. However, recent advances in ion-beam microtexturing now enable another aspect of the invention, namely the manufacture of adjacent regions of very high and very low emissivity in a complex pattern of very closely controlled characteristics.

Figure 17A:
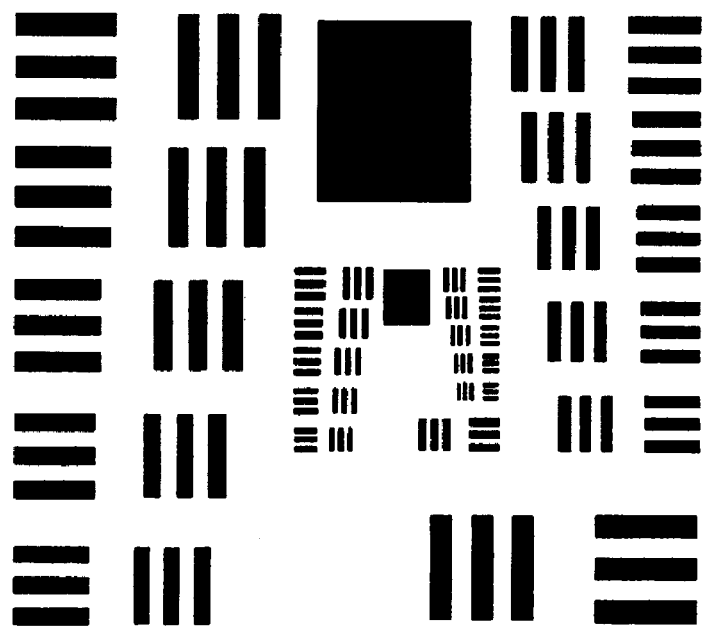
FIGS. 17A and 17B show an exemplary resolution test pattern and a resolution tester respectively for the invention.
Figure 17B:
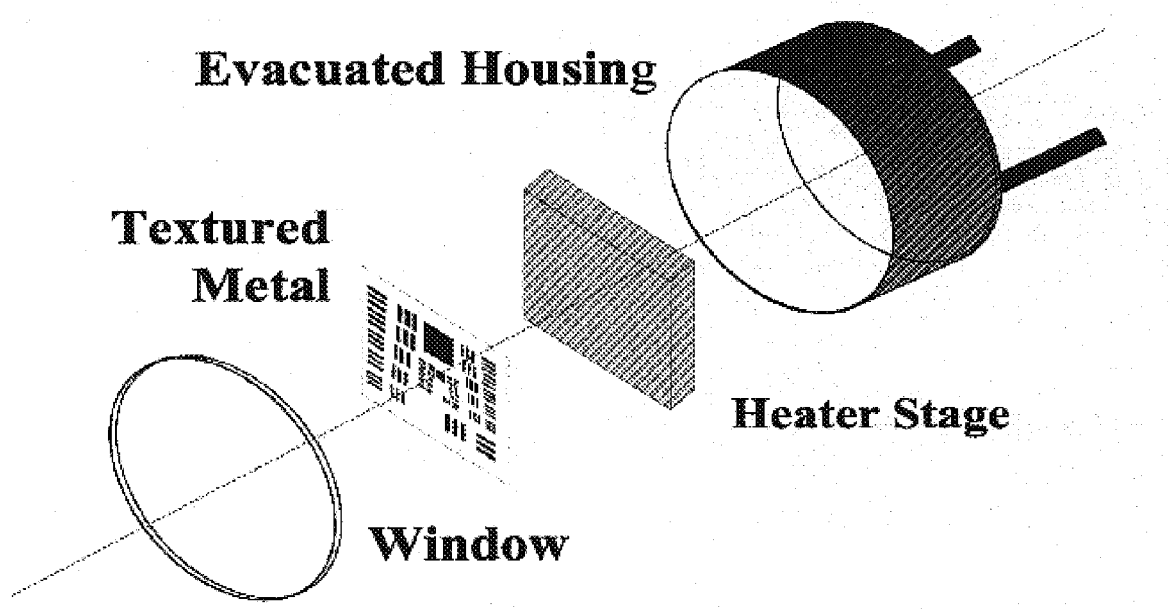

FIG. 17A shows a resolution test pattern and FIG. 17B shows a resolution tester. By using ion beam lithography techniques, alternating bands of very high and very low emissivity are established on a lightweight, high conductivity metal foil surface. Using a tiny thermoelectric hot/cold stage to uniformly vary the temperature of this test pattern permits simultaneous radiometric and resolution tests.

Modern high-performance IR systems have narrow fields of view, consequently long focal lengths and very high resolution. This complicates the problem of designing a built-in resolution tester, since calibration objects must appear to be very far away. In a conventional test arrangement, a collimator is used to project the image of the blackbody source with a slit pattern onto the aperture of the system under test. In this arrangement, the collimator acts as one lens and the fore-optics as another; the magnification of this two lens system is the focal length ratio of the two lenses. This means that, to project very small test patterns onto the focal plane array under test, either the test target itself must be very small or the collimator must have a much longer focal length than the fore-optics of the system under test. A test object of the invention has extremely fine lines and spaces, as the key to calibrating high resolution systems with a device of modest size. In one form, the invention includes a three-element, germanium f/1 lens system adapted from the "IR microcam," to build a hand-held external test device.

Figure 18A:
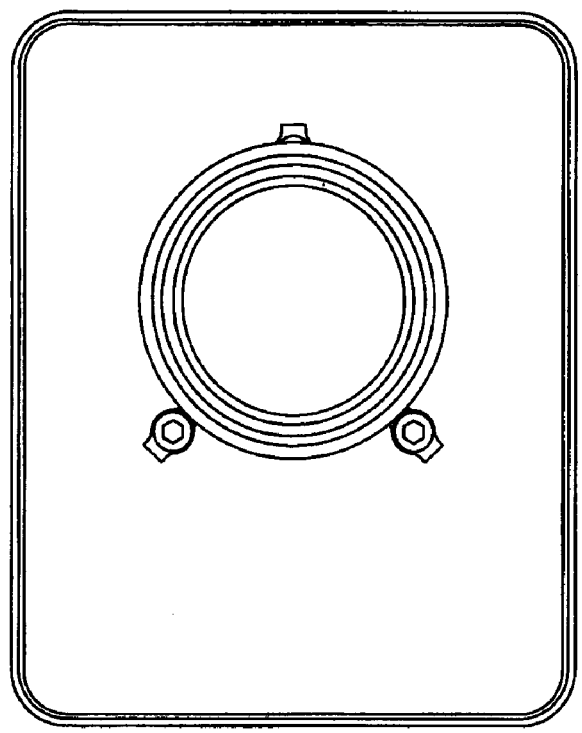
FIGS. 18 and 18B show an exemplary system of the invention.
Figure 18B:
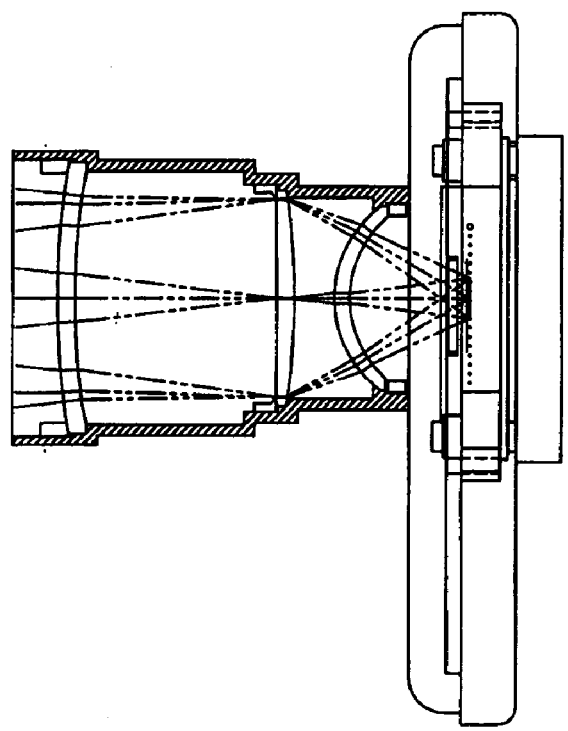

FIGS. 18A and 18B shows the IR scam lens as a 3-element germanium f/1 system. It has a 25 mm aperture. It provides night vision capability for hand-launched unmanned aircraft (HL-UAV). This optical train is the basis of a hand-held resolution tester.

FPA Health Check Source

Like most infrared seekers, gain and offset in the AIT seeker depend on the local temperature (and pixel-to-pixel temperature variations) on the focal plane array. One way to compensate for gain and offset variations is to use a flat-field IR reference source to provide uniform illumination on all pixels before (or during) flight. Such a source would also be extremely useful for an FPA health check on a Dem-Val flight. The metal texturing technology developed by the M&S program makes it possible to build extremely compact, lightweight infrared reference sources. Another aspect of the invention is an MWIR reference source for the BMDO STRV-2 mission. The STRV-2 source is very small (6 mm diameter×3 mm thick) since it was designed to go on the filter wheel very close to the FPA.

Changes in the STRV-2 orbital and mission profiles meant that its original cryocooler was replaced with a more robust, but vibrationally noisier, cooler. Although this solved some thermal problems for the MWIR telescope, it meant that the telescope had to take its images with the cooler switched off. The new orbit, inclined nearly 65 degrees, will allow the telescope to see the sun for nearly half of every orbit so that the telescope must be designed to operate accurately even when it is not in thermal equilibrium. This will require on-station calibration. But, because weight and space are at a premium within the MWIR payload, a conventional blackbody source was not practical.

Figure 19A:
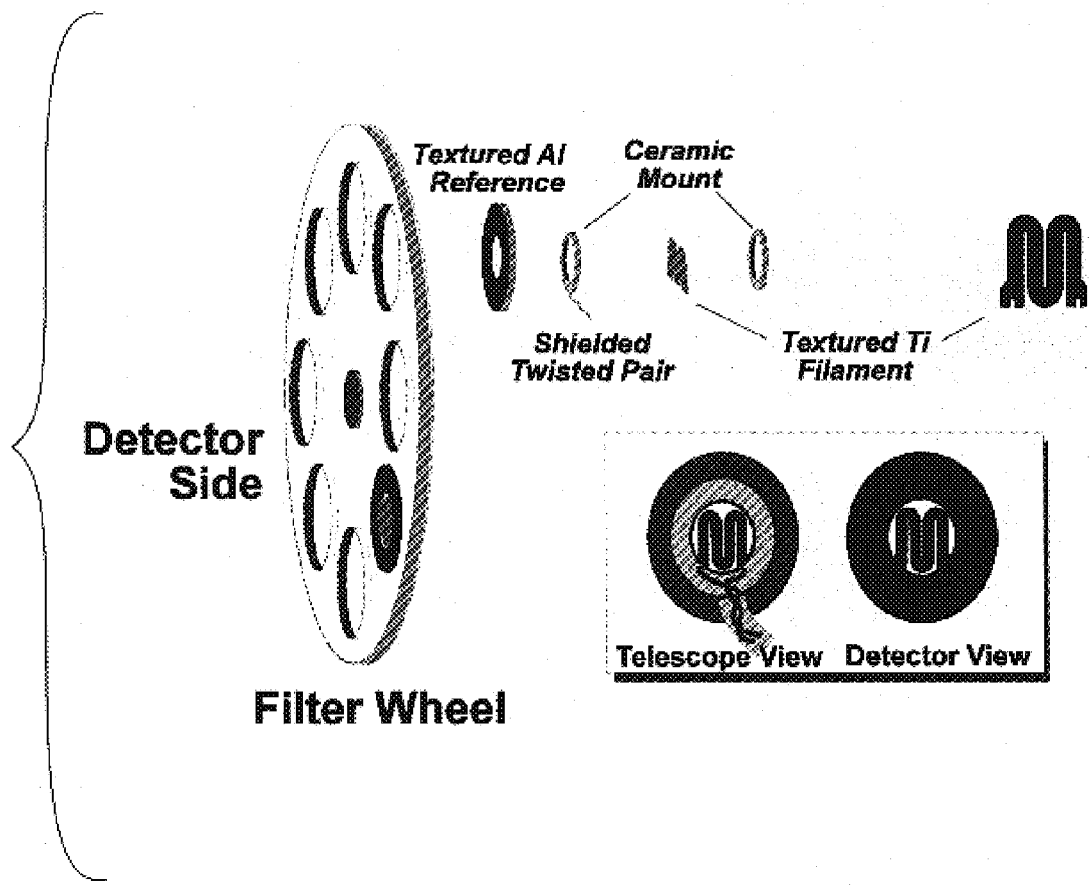
FIG. 19A shows an exemplary reference source according to the invention in a filter wheel slot.
Figure 19B:
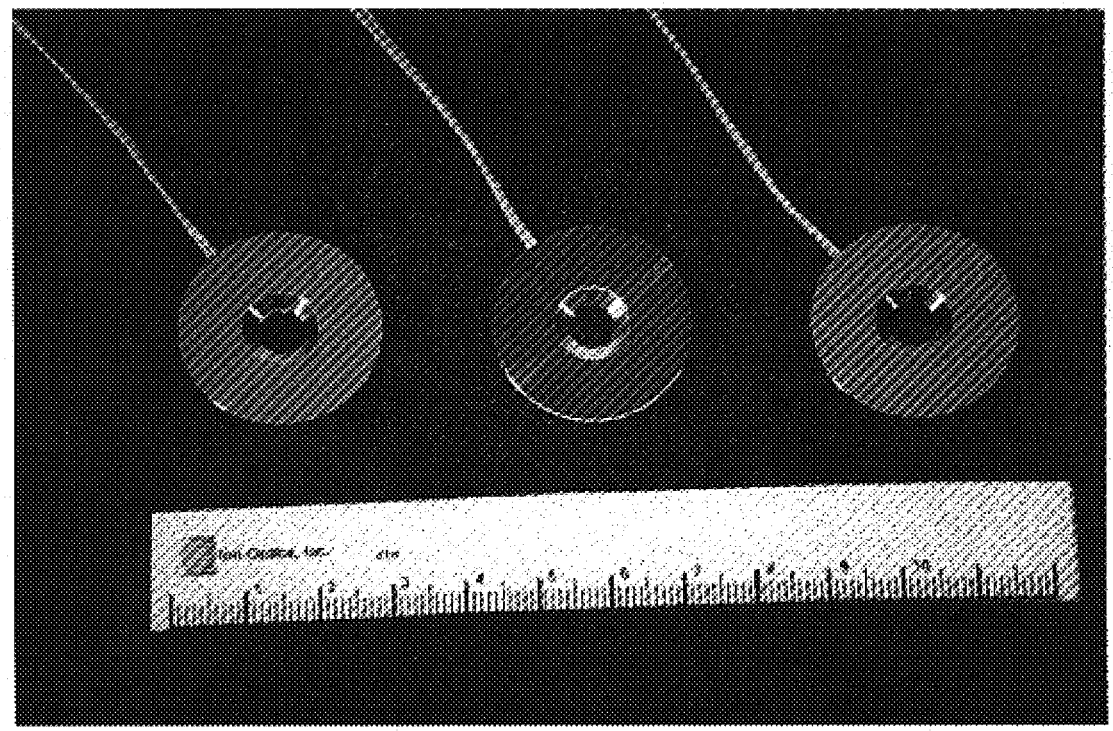
FIG. 19B shows exemplary signal sources adjacent to a metric.

FIG. 19A shows a prototype reference source for STRV-2, mounted in an existing filter wheel slot for minimum design and schedule impact. This source provides flat-fielding to correct pixel-to-pixel offset variations. FIG. 19B shows exemplary sources adjacent to a metric.

This simple modular device provides a flat field warm-body reference with no parasitic heating of the optical train and it will allow correction of pixel-to-pixel offset variations on the focal plane.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein

The invention claimed is:

1. A narrow band incoherent radiation emitter detector comprising:
a planar filamental emission/detection element characterized by a predetermined spectral range of emitted/detected radiation and a emission/detection width of dl/1 less than about 0.1, where 1 is the wavelength of said radiation, wherein said emission/detection width is substantially determined by surface features of said emission/detection element.

2. An emitter detector to claim 1 wherein said spectral range includes relatively long wavelengths and excludes relatively short wavelengths.

3. An emitter/detector according to claim 2 wherein said emission/detection width is substantially determined by surface features of said emission/detection element.

4. An emitter/detector according to claim 1 wherein said spectral range is near an infrared absorption line of a predetermined material.

5. An emitter/detector according to claim 4 wherein said emission/detection width is substantially determined by surface features of said emission/detection element.

6. An emitter/detector according to claim 1 wherein said spectral range excludes relatively long wavelengths and relatively short wavelengths and includes a range of intermediate wavelengths therebetween.

7. An emitter/detector according to claim 6 wherein said range of intermediate wavelengths includes an infrared absorption line of a predetermined material.

8. An emitter/detector according to claim 6, further comprising a thermal detector for photons characterized by a wavelength within said intermediate range.

9. An emitter/detector according to claim 6 further comprising a thermal detector for detecting Infrared energy characterized by a wavelength in said intermediate range.

10. An emitter/detector according to claim 6 wherein said emission/detection element is a suspended filament made of a metal foil.

11. An emitter/detector according to claim 6 wherein said emission/detection element is suspended filament made of a back-etched semiconductor.

12. An emitter/detector according to claim 6 wherein said emission/detection element is a resistive element having an emission surface to control said spectral range.

13. A gas detector comprising:
  A. a planar filamental emission/detection element characterized by a predetermined spectral range of emitted/detected radiation and a emission/detection width dl/1 less than about 0.1, where 1 is the wavelength of said radiation, wherein said emission/detection width is substantially determined by surface features of said emission/detection element, said emission/detection element having an input/output axis, and
  B. a first reflector disposed along said input/output axis and opposite to said emission/detection element, whereby an optical path is defined from said emission/detection element to said first reflector to and back to said emission/detection element, wherein said optical path between said emission/detection element and said first reflector passes through a gas test region.

14. A gas detector according to claim 13, further comprising:
  C. a driver for driving said emission/detection element to emit radiation propagating along said optical path toward said first reflector.

15. A gas detector according to claim 12 further comprising:
  D. a processor responsive to said emission/detection element for generating an output signal representative of radiation incident thereon.

16. A gas detector according to claim 13 wherein said spectral range includes a wavelength corresponding to an absorption line of a predetermined gas.

17. A gas detector according to claim 13 further comprising:
  a second reflector extending from points near said emission/detection element along said input/output axis,
  wherein said second reflector is disposed along said optical path, whereby said optical path extends from said emission/detection element to said second reflector to said first reflector to said second reflector to said emission/detection element, and wherein said optical path between said second reflector and said first reflector passes through said gas test region.

18. A gas detector according to claim 17, further comprising:
  C. a driver for driving said emission/detection element to emit radiation propagating along said optical path toward said first reflector.

19. A gas detector according to claim 18 further comprising:
  D. a processor responsive to said emission/detection element for generating an output signal representative of radiation incident thereon.

20. A gas detector according to claim 17 wherein said second reflector is a beam-forming reflector and said second reflector is substantially planar.

21. A gas detector comprising:
  A. a planar filamental emission element characterized by a predetermined spectral range of emitted radiation and an emission width dl/1 less than about 0.1, where 1 is the wavelength of said emission element having an output axis, wherein said emission width is substantially determined by surface features of said emission/detection element,
  B. a first reflector disposed along said output axis, and
  C. a planar filamental detection element characterized by a predetermined spectral range of detected radiation and an emission/detection width dl/1 less than about 0.1, where 1 is the wavelength of said detection element having an input axis, whereby an optical path is defined from said emission element to said first reflector and to said first detection element, wherein said optical path between said emission element and said first reflector, or between said first reflector and said detection element or both, passes through a gas test region.

22. A gas detector according to claim 21 further comprising:
  a second reflector disposed along said optical path between said first reflector and said detection element whereby said optical path extends from said emission element to said first reflector to said reflector to said detection element, and wherein said optical path between said first reflector and said second reflector passes through said gas test region.

23. A gas detector according to claim 21, further comprising:
  C. a driver for driving said emission element to emit radiation propagating along said optical path toward said first reflector.

24. A gas detector according to claim 21 further comprising:
  D. a processor responsive to said detection element for generating an output signal representative of radiation incident thereon.

25. A gas detector according to claim 21 wherein said spectral range includes a wavelength corresponding to an absorption line of a predetermined gas.

26. A multi-wavelength radiation emitter/detector array comprising:
  an array of planar emission/detection elements, each element being characterized by a predetermined spectral range of emitted/detected radiation and an emission/detection width dl/1 less than about 0.1, when 1 is the wavelength of said radiation, wherein each emission/detection width is substantially determined by surface features of each respective emission/detection element.

27. An array according to claim 26 wherein said array is adopted to emit/detect information representative of a planar image.

* * * * *